(12) United States Patent
Semba et al.

(10) Patent No.: US 7,078,225 B2
(45) Date of Patent: Jul. 18, 2006

(54) METHOD FOR ENZYMATICALLY PRODUCING AN OPTICALLY ACTIVE CYANOHYDRIN

(75) Inventors: Hisashi Semba, Ibaraki (JP); Yukio Dobashi, Ibaraki (JP)

(73) Assignee: Nippon Shokubai Co., Ltd., Osaka (JP)

(*) Notice: Subject to any disclaimer, the term of this patent is extended or adjusted under 35 U.S.C. 154(b) by 23 days.

(21) Appl. No.: 09/870,821

(22) Filed: Jun. 1, 2001

(65) Prior Publication Data

US 2002/0006646 A1 Jan. 17, 2002

(30) Foreign Application Priority Data

| Jun. 2, 2000 | (JP) | ................................ 2000-166578 |
| Jun. 2, 2000 | (JP) | ................................ 2000-166579 |
| Jul. 7, 2000 | (JP) | ................................ 2000-206130 |

(51) Int. Cl.
  *C12P 13/00* (2006.01)

(52) U.S. Cl. ........................................ 435/280; 435/128

(58) Field of Classification Search ................. 435/128, 435/280

See application file for complete search history.

(56) References Cited

U.S. PATENT DOCUMENTS

| 4,859,784 | A | 8/1989 | Effenberger et al. |
| 5,008,192 | A | 4/1991 | Neidermeyer et al. |
| 5,350,871 | A | 9/1994 | Geluk et al. |
| 6,225,095 | B1 | 5/2001 | Pochlauer et al. |
| 6,337,196 | B1 * | 1/2002 | Kirchner et al. ............. 435/128 |

FOREIGN PATENT DOCUMENTS

| EP | 0 547 655 A | 6/1993 |
| JP | 03-287559 | 12/1991 |
| JP | 04-342588 | 11/1992 |
| WO | 98/30711 | * 7/1998 |

OTHER PUBLICATIONS

Dove, S. et al., 7–Substituted–4–hydroxyquinoline–3–carboxylic Acids as Inhibitors of Dehydrogenase Enzymes and of the Respiration of Ehrlich Ascites Tumor Cells: Multivarite Analysis and Quantitlative Structure–Activity Relationship for Polar Substituents, *J. Med. Chem.*, 1985, vol. 28, pp. 447–451.

Notice of Rejection dated Mar. 8, 2005 in Japanese Application No. 2000–206130.

Loos et al. "Synthesis of Optically Active Cyanohydrins Using R–Oxynitrilase in a Liquid–Liquid Biphasic System," *Biocatalysis and Biotransformation*, vol. 12, 255–266 (1955).

Wehtje et al. "Activity and operational stability of immobilized mandelonitrile lyase in methanol/water mixtures," *Appl. Microbiol. and Biotechno.*, vol. 29, 419–425 (1988).

* cited by examiner

*Primary Examiner*—Sandra E. Saucier
(74) *Attorney, Agent, or Firm*—Finnegan, Henderson, Farabow, Garrett, & Dunner, L.L.P.

(57) ABSTRACT

The present invention relates to an enzyme reaction method which comprises performing an enzyme reaction, using an immobilized enzyme having a water content of 10% by weight or more as an enzyme and using an organic solvent substantially immiscible with water as a reaction solvent, under such conditions that a liquid phase forms a homogeneous system without phase separation although it is saturated with water or an aqueous buffer; a method for performing an enzyme reaction using an aldehyde compound as a substrate, which comprises removing a carboxylic acid compound contained in an aldehyde compound by subjecting the aldehyde compound to an alkaline treatment before starting the enzyme reaction; a method for performing an enzyme reaction using an aldehyde compound as a substrate, which comprises reducing a carboxylic acid compound content in the aldehyde compound to 0.1 wt % or less by subjecting the aldehyde compound to an alkaline treatment before starting the enzyme reaction; a method for enzymatically producing an optically active cyanohydrin from a carbonyl compound and prussic acid containing an acidic substance as a stabilizer, which comprises subjecting the prussic acid to a treatment for reducing inhibitory effect of the stabilizer on an enzyme, and performing an enzyme reaction to synthesize the optically active cyanohydrin using the treated prussic acid; a method for enzymatically producing an optically active cyanohydrin, which comprises dissolving prussic acid in an organic solvent substantially immiscible with water to give an organic solution of prussic acid, adding a buffer to this solution in a saturation amount or more, mixing, collecting the organic phase, and performing an enzyme reaction to synthesize the optically active cyanohydrin using the organic phase as prussic acid; as well as a method for enzymatically producing an optically active cyanohydrin, which comprises performing distillation of a reaction solution after completion of an enzyme reaction to separate and collect unreacted prussic acid and organic solvent therefrom, and repeatedly using the collected prussic acid and organic solvent at least once.

4 Claims, 4 Drawing Sheets

F I G. 4
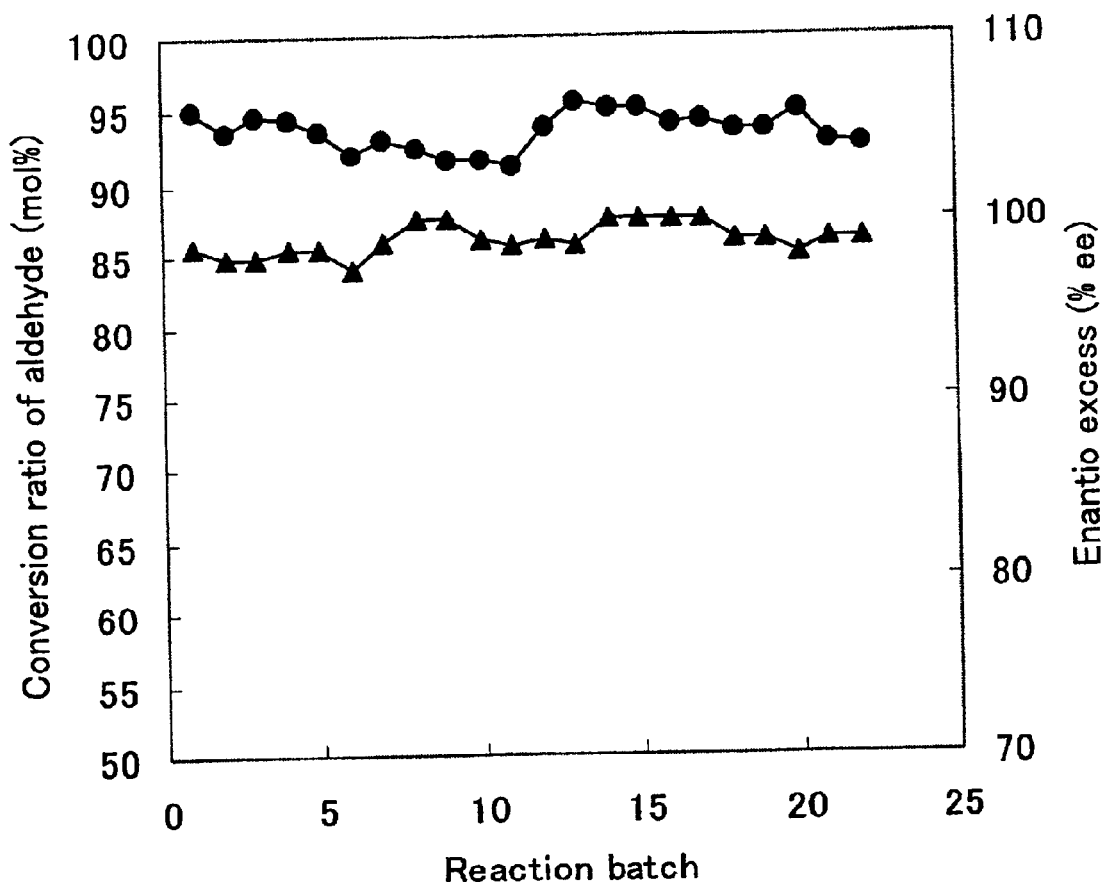

METHOD FOR ENZYMATICALLY PRODUCING AN OPTICALLY ACTIVE CYANOHYDRIN

BACKGROUND OF THE INVENTION

The present invention relates to an enzyme reaction method and a method for enzymatically producing an optically active cyanohydrin.

An enzyme reaction advantageously uses an organic solvent as a reaction solvent so as to increase the concentration of a substrate or product that is hard to dissolve in water. Such an enzyme reaction in an organic solvent has therefore been used as a reaction system for various enzymes. However, in contrast to an aqueous environment in which an enzyme is stable and active, an enzyme is often denatured and thus generally unstable in an organic solvent system. For this reason, in cases where enzyme reactions are applied to industrial syntheses of useful substances, the construction of reaction systems depends on the nature of enzymes to be used. A choice between high concentration reaction conditions and the stability of enzyme is therefore made according to individual circumstances. Particularly, in a method wherein hydroxynitrile lyase catalyzes the synthesis of an optically active cyanohydrin from hydrogen cyanide and a carbonyl compound as substrates, this enzyme is relatively stable in an organic solvent, but it provides a significant decrease in reaction rate when water is absent from the reaction system. Accordingly, such a conventionally known reaction using hydroxynitrile lyase in an organic solvent system involves a problem of extended reaction time. In addition, an aromatic carbonyl compound used as a substrate for this enzyme has low solubility in water, so that it is not practical to carry out such a reaction in an aqueous system due to low substrate and product concentrations.

With regard to the synthesis of an optically active cyanohydrin in the presence of hydroxynitrile lyase, the following reaction systems have been reported: an aqueous system, i.e., a system which uses water or an aqueous buffer containing an enzyme and a substrate dissolved therein (Japanese Patent Examined Publication No. 07-53116); a mixed solvent system comprising a mixture of a polar solvent and water (Appl. Microbiol. Biotechnol., Vol. 29, 419–425, 1988); an organic solvent system saturated with water or an aqueous buffer (Japanese Patent Laid-Open Publication No. 63-219388); and a two-phase system comprising a mixture of an organic solvent with water or an aqueous buffer at a volume ratio of 1/5 to 5/1 (Japanese Patent Laid-Open Publication No. 05-317065; Biocatal. Biotrans. Vol. 12, 255–266, 1995; Japanese Patent Laid-Open Publication No. 11-243983).

An aqueous reaction system involves a problem of insufficient efficiency attributed to low substrate and product concentrations because a carbonyl substrate, such as aldehyde or ketone, generally has low solubility in water. A mixed solvent system comprising a mixture of a polar solvent and water also involves a problem of insufficient efficiency although it provides some increases in substrate concentration, as compared with a simple aqueous system. This system involves an additional problem that a polar solvent is likely to affect the stability of the enzyme. The use of an organic solvent saturated with water or an aqueous buffer achieves higher substrate and product concentrations, but on the other hand, it provides a low reaction rate because the water content is too low. A two-phase system comprising an organic solvent and water is advantageous in improving a reaction rate and in increasing substrate and product concentrations. In practice, however, an enzyme comes into direct contact with an organic solvent in this system, so that the enzyme and contaminant proteins are likely to be denatured by the organic solvent. The denatured proteins may affect separation at the interface between organic and aqueous phases and, in some cases, may result in an emulsified reaction mixture. The two-phase system therefore involves difficulties of the separation of a reaction mixture into two phases.

An enzyme reaction using an aldehyde compound as a substrate is a widely carried out reaction. In particular, an enzyme reaction for synthesizing an optically active cyanohydrin from an aldehyde compound and hydrogen cyanide as substrates is useful because this reaction enables efficient synthesis of an optically active cyanohydrin which is difficult to chemically synthesize.

Thus, the above reaction is very advantageous, but it is known that, for example, the synthesis of (R)-mandelonitrile from benzaldehyde in the presence of (R)-hydroxynitrile lyase as a catalyst is inhibited when benzaldehyde as a starting material is contaminated by benzoic acid. However, there is no knowledge regarding acceptable concentration and effective removal of impurities such as benzoic acid, which act as inhibitors against enzyme reactions.

Impurities present in a starting aldehyde compound may be removed by distillation. However, distillation is not easily applied to industrial processes because it requires a distillation plant, it cannot completely separate some impurities such as benzoic acid due to their sublimation properties, and it may accelerate the production of carboxylic acids due to the application of heat. It has been therefore desirable to develop an enzyme reaction method that achieves simple and effective removal of impurities and thereby provides a product of interest in high yield.

There have been many reports about reactions for the synthesis of an optically active cyanohydrin from a carbonyl compound and prussic acid in the presence of an enzyme catalyst such as hydroxynitrile lyase. However, none of these reports has mention an industrially produced prussic acid containing a stabilizer which seriously affects the activity of hydroxynitrile lyase. There are two possible reasons for this. First, the previous reports took little notice of the above fact because prussic acid used therein was prepared for laboratory use in a very small amount, but not industrially produced, so that it contained no stabilizer. Second, the above fact did not present a problem in cases where prussic acid was added to a reaction system at low concentration the stabilizer hardly affected the reaction.

Further, when an optically active cyanohydrin is synthesized from a carbonyl compound and prussic acid (starting materials) in an organic solvent (reaction solvent) in the presence of hydroxynitrile lyase as a catalyst, the resulting reaction product is dissolved in the organic solvent used as a reaction solvent.

To collect the optically active cyanohydrin produced in this reaction, in general, there is a need to remove low-boiling solvents by distillation from the reaction product solution containing the optically active cyanohydrin. However, recycling of the distillate was previously unknown although collection of an optically active cyanohydrin through distillation of a reaction product solution is a known process.

OBJECTS AND SUMMARY OF THE INVENTION

In the first aspect, the present invention provides an immobilized enzyme reaction system in which a product of interest can be synthesized at a high concentration and at a sufficient reaction rate.

In the second aspect, the present invention provides an enzyme reaction method using an aldehyde compound as a substrate, which achieves removal of an inhibitor against the enzyme reaction and thereby provides a product of interest in high yield.

In the third aspect, the present invention provides an industrially advantageous method for synthesizing an optically active cyanohydrin from a carbonyl compound and prussic acid in the presence of an enzyme catalyst such as hydroxynitrile lyase.

In the fourth aspect, the present invention provides the effective use of a reaction solvent and unreacted prussic acid in a method for producing an optically active cyanohydrin.

Our research efforts were directed to overcoming the above problems, and we have found that the use of an immobilized enzyme having a water content of 10% by weight or more in combination with a substrate-containing organic solvent saturated with water or an aqueous buffer enables the construction of a reaction system which permits a reaction at a high reaction rate and at a high concentration, and very simple separation and recovery of the enzyme from the reaction mixture after the reaction, thereby finally completing the first aspect of the present invention.

Namely, the first aspect of the present invention encompasses the following embodiments.

(1) An enzyme reaction method which comprises performing an enzyme reaction, using an immobilized enzyme having a water content of 10% by weight or more as an enzyme and using an organic solvent substantially immiscible with water as a reaction solvent, under such conditions that a liquid phase forms a homogeneous system without phase separation although it is saturated with water or an aqueous buffer.

(2) A method according to (1) above, wherein an enzyme comprising immobilized hydroxynitrile lyase which catalyzes the synthesis of a cyanohydrin from hydrogen cyanide and a carbonyl compound is used as the immobilized enzyme to convert the carbonyl compound into the corresponding optically active cyanohydrin.

(3) A method according to (2) above, wherein hydroxynitrile lyase is (R)-hydroxynitrile lyase or (S)-hydroxynitrile lyase, and an asymmetric carbonyl compound is converted into the corresponding optically active cyanohydrin.

(4) A method according to any one of (1) to (3) above, wherein a carrier capable of retaining water is used as a carrier for the immobilized enzyme.

(5) A method according to any one of (1) to (4) above, wherein the reaction is carried out under such conditions that a liquid phase contains water in a saturation amount in order to prevent the release of water from the immobilized enzyme into the liquid phase during the reaction.

In the first aspect, the present invention not only increases the substrate and product concentrations because the reaction uses a homogeneous system of organic solvent, but also improves the activity and stability of the enzyme because the enzyme is present within a carrier for immobilization having a sufficient water content. Further, the present invention is characterized by a simple separation of the enzyme from the reaction mixture through solid-liquid separation since the reaction mixture can be kept clear without emulsification. A reaction in an organic solvent system containing water in a trace amount is generally called an enzyme reaction in an organic solvent-trace aqueous system. The water content in this case is normally at most several percent. In contrast, in the present invention, there is no upper limit on water content relative to the whole reaction system, so long as water is not released from the immobilized enzyme to form an aqueous phase in the reaction mixture and thereby produce two separated phases. Unlike the above organic solvent-trace aqueous system, an enzyme reaction in the present invention favours a higher water content of 10% by weight or more in the immobilized enzyme. The present invention is therefore completely different from the conventional organic solvent-trace aqueous system.

In the first aspect, the present invention can also be particularly and preferably applied to a reaction in which hydroxynitrile lyase catalyzes the synthesis of an optically active cyanohydrin from a carbonyl compound and hydrogen cyanide.

In addition, we have found that in an enzyme reaction using an aldehyde compound as a substrate, the reaction is inhibited by a carboxylic acid compound which is present in and corresponds to the aldehyde compound.

We have now found that an alkaline treatment of an aldehyde compound achieves simpler and more certain removal of such an inhibitor ensuring successful use of a lower-grade aldehyde compound in the enzyme reaction, thereby finally completing the second aspect of the present invention.

Namely, the second aspect of the present invention encompasses the following embodiments.

(1) A method for performing an enzyme reaction using an aldehyde compound as a substrate, which comprises removing a carboxylic acid compound contained in an aldehyde compound by subjecting the aldehyde compound to an alkaline treatment before starting the enzyme reaction.

(2) A method for performing an enzyme reaction using an aldehyde compound as a substrate, which comprises reducing a carboxylic acid compound content in the aldehyde compound to 0.1 wt % or less by subjecting the aldehyde compound to an alkaline treatment before starting the enzyme reaction.

(3) A method according to (1) or (2) above, wherein the alkaline treatment comprises mixing the aldehyde compound with an alkaline aqueous solution and then separating the aldehyde compound from the aqueous phase.

(4) A method according to any one of (1) to (3) above, wherein the enzyme reaction is the synthesis of an optically active cyanohydrin from the aldehyde compound and hydrogen cyanide in the presence of hydroxynitrile lyase as a catalyst.

Further, our research efforts were directed to overcoming the above problems, and we have found that an acidic substance (e.g., sulfurous acid or sulfuric acid) included as a stabilizer in an industrially available prussic acid inhibits the activity of an enzyme such as hydroxynitrile lyase and that the reduction of the stabilizer's inhibitory effect provides an significantly extended life-time of an enzyme such as hydroxynitrile lyase, thereby finally completing the third aspect of the present invention.

Namely, the third aspect of the present invention encompasses the following embodiments.

(1) A method for enzymatically producing an optically active cyanohydrin from a carbonyl compound and prussic acid containing an acidic substance as a stabilizer, said prussic acid providing an aqueous phase with pH 5 or less when dissolved at a concentration of 1.5 M in an organic solvent substantially immiscible with water, mixed with pure water at such a ratio that the mixture separates into organic and aqueous phases, and then allowed to stand, wherein said method comprises:
  subjecting the prussic acid to a treatment for reducing inhibitory effect of the stabilizer on an enzyme; and
  performing an enzyme reaction to synthesize the optically active cyanohydrin using the treated prussic acid.
(2) A method for enzymatically producing an optically active cyanohydrin from prussic acid and a carbonyl compound, which comprises:
  dissolving prussic acid in an organic solvent substantially immiscible with water to give an organic solution of prussic acid;
  adding a buffer to this solution in a saturation amount or more;
  mixing;
  collecting the organic phase; and
  performing an enzyme reaction to synthesize the optically active cyanohydrin using the organic phase as prussic acid.
(3) The method according to (2) above, wherein the buffer has buffering ability in a range of pH 4 to pH 7.
(4) The method according to any one of (1) to (3) above, wherein the enzyme reaction is catalyzed by hydroxynitrile lyase.

Furthermore, we have found that reduced-pressure distillation of a reaction solution containing an optically active cyanohydrin synthesized in an enzyme reaction using hydroxynitrile lyase can provide very effective collection of not only a reaction solvent but also unreacted prussic acid and that the solution thus collected can be re-used for the enzyme reaction, thereby finally completing the fourth aspect of the present invention.

Namely, the fourth aspect of the present invention encompasses the following embodiments.
(1) A method for enzymatically producing an optically active cyanohydrin from prussic acid and a carbonyl compound, which comprises:
  performing distillation of a reaction solution after completion of an enzyme reaction to separate and collect unreacted prussic acid and organic solvent therefrom; and
  repeatedly using the collected prussic acid and organic solvent at least once.
(2) The method according to (1) above, wherein the reaction solution after completion of an enzyme reaction is obtained from the method of the first, second or third aspect of the present invention.

Any enzyme may be used in the first aspect of the present invention without particular limitations, so long as it can provide an improved reaction efficiency in a reaction system in which an organic solvent is used as a reaction solvent. Such an enzyme may be an enzyme catalyst whose substrate is a compound hard-to-dissolve or insoluble in water. Illustrative examples includes oxidase or reductase, such as monooxygenase, which catalyzes the oxidation-reduction of an aromatic compound; an ester-hydrolyzing enzyme, such as esterase, which catalyzes the synthesis and/or substitution of an ester compound; glycosyltransferase, such as glucosidase, which catalyzes the glycosylation of a compound hard-to-dissolve or insoluble in water; nitrile hydratase which hydrolyzes a nitrile compound; and hydroxynitrile lyase which catalyzes the synthesis of an optically active cyanohydrin from a carbonyl substrate easily soluble in an organic solvent. In particular, it is preferable to use hydroxynitrile lyase which catalyzes the synthesis of an optically active cyanohydrin.

The above-mentioned hydroxynitrile lyase means an enzyme catalyzing the synthesis of an optically active cyanohydrin from hydrogen cyanide and a carbonyl compound. Hydroxynitrile lyase for the synthesis of (R)-cyanohydrin (hereinafter, (R)-hydroxynitrile lyase) includes those derived from Rosaceae plants such as almond (*Prunus amygdalus*) and Linaceae plants. Hydroxynitrile lyase for the synthesis of (S)-cyanohydrin (hereinafter, (S)-hydroxynitrile lyase) includes those derived from Gramineae plants such as sorghum (*Sorghum bicolor*), Euphorbiaceae plants such as *Manihot esculenta* and *Hevea brasiliensis*, and Olacaceae plants such as *Ximenia americana*.

The above enzyme may be prepared by extraction from organism's tissues containing the enzyme. Alternatively, the enzyme may also be produced from a recombinant organism into which a cloned gene of the enzyme has been introduced. Furthermore, any hydroxynitrile lyase having an altered enzyme action, which is created by modifying the wild-type hydroxynitrile lyase gene, may be used in the present invention, so long as it retains the above activity.

In the first aspect, the present invention uses a carrier for immobilization as a support to hold enzyme molecules and to retain water. Any carrier may be used without particular limitations, so long as it can hold enzyme molecules and retain water. A preferred carrier may be one which is hydrophilic or one which retains water or an aqueous buffer therein, for example, a porous inorganic carrier, a water-retaining carrier based on fibers such as cellulose, or a carrier made of a polymer compound(s). Specific examples include, but are not limited to, inorganic carriers such as porous ceramic particles, porous silica gel particles and zeolite particles; natural polymer gels such as agar, calcium alginate and chitosan; and synthetic polymer gels such as polyacrylic acid, polyacrylamide and polyvinyl alcohol.

In the first aspect of the present invention, enzyme molecules may be immobilized in any manner, for example, by allowing carriers to absorb an enzyme solution, by mixing carriers with an enzyme solution to immobilize enzyme molecules on/in the carriers by absorption, by entrapping and immobilizing enzyme molecules within carriers, or by cross-linking enzyme molecules via crosslinkers.

In the first aspect of the present invention, it is important to adjust the water content of the immobilized enzyme such that the water content (%) relative to the whole reaction system (comprising the immobilized enzyme, water or an aqueous buffer, a solvent, a substrate and a product) is greater than a saturation amount (%) of water dissolvable in a reaction solvent containing the substrate and/or product.

At the water content as little as the above saturation amount, the enzyme is not substantially surrounded with water, leading to a significant decrease in reaction rate. On the other hand, when water is given in an amount far in excess of that which can be retained within the immobilized enzyme, a liquid phase is separated into two phases, i.e., organic and aqueous phases. This makes the immobilized enzyme less dispersible in the reaction solvent, leading to a decrease in reaction efficiency.

In practice, the amount of water soluble in a solvent will vary depending on the type of solvent to be used and conditions for temperature and substrate concentration. It is therefore desirable to select the water content appropriately according to reaction conditions to be applied.

In the first aspect of the present invention, an organic solvent substantially immiscible with water is used as a reaction solvent in order to improve the concentration of starting materials and productivity. As used herein, an "organic solvent substantially immiscible with water" means an organic solvent except for those soluble in water in any proportion. Any solvent may be used as an organic solvent without particular limitations, so long as it is substantially immiscible with water and has no influence upon an enzyme reaction. For example, a solvent to be used in the synthesis of an optically active cyanohydrin catalyzed by hydroxynitrile lyase may be selected appropriately according to the nature of aldehyde or ketone to be used as a starting material for the synthesis and the nature of cyanohydrin obtainable as a reaction product.

Specific examples of an organic solvent substantially immiscible with water include optionally halogenated hydrocarbon solvents such as saturated or unsaturated linear, branched or cyclic aliphatic hydrocarbons and aromatic hydrocarbons, for example, pentane, hexane, cyclohexane, benzene, toluene, xylene, methylene chloride and chloroform; optionally halogenated alcoholic solvents such as saturated or unsaturated linear, branched or cyclic aliphatic alcohols and aralkyl alcohols, for example, n-butanol, isobutanol, t-butanol, hexanol, cyclohexanol and n-amyl alcohol; optionally halogenated ether solvents such as saturated or unsaturated linear, branched or cyclic aliphatic ethers and aromatic ethers, for example, diethyl ether, dipropyl ether, diisopropyl ether, dibutyl ether, t-butyl methyl ether and dimethoxyethane; and optionally halogenated ester solvents such as saturated or unsaturated linear, branched or cyclic aliphatic esters and aromatic esters, for example, methyl formate, methyl acetate, ethyl acetate, butyl acetate and methyl propionate. These solvents may be used alone or in combination.

In some cases, an organic solvent merely saturated with water or an aqueous buffer may increase its solubility in water upon a substrate is dissolved in this solvent, resulting in the loss of water from the immobilized enzyme. In such a case where a substrate having the nature as mentioned above is used for the reaction, the saturation treatment with water or an aqueous buffer may be preferably carried out after the substrate is dissolved in the organic solvent.

For example, in the synthesis of an optically active cyanohydrin using prussic acid as a substrate, the saturation treatment with water or an aqueous buffer may be preferably carried out after prussic acid is dissolved in an organic solvent. That is, prussic acid may be dissolved in the organic solvent at a given concentration, which may then be mixed with a saturation amount of water or an aqueous buffer. Alternatively, the organic solvent and the substrate may be added to the reaction system before the saturation treatment, followed by addition of water or an aqueous buffer in a saturation amount which has been determined by measuring an amount of water soluble in the organic solvent containing the substrate dissolved therein. An aqueous buffer used here may be any buffer adjusted to around an optimum pH of an enzyme reaction, for example, a buffer prepared from a salt such as phosphate, citrate, glutarate, malate, malonate, o-phthalate or succinate.

By way of example, the construction of a reaction system for synthesizing an optically active cyanohydrin will be presented below. This reaction system uses t-butyl methyl ether as a reaction solvent, 1 M benzaldehyde and 1.5 M prussic acid (hydrocyanic acid) as substrates, and immobilized hydroxynitrile lyase as a catalyst. The synthesis is carried out at a reaction temperature of about 20° C.

1. Preparation of Immobilized Enzyme

An immobilized enzyme having a water content of 10% by weight or more is prepared by introducing carriers for immobilization into an enzyme solution to immobilize enzyme molecules on/in the carriers by absorption, or by mixing the carriers with the enzyme solution in an amount equal to or less than that of water which can be retained within the carriers. The water content in this case may vary widely, so long as water can be retained within the immobilized enzyme, that is, a liquid phase can form a homogeneous system of organic solvent. It preferably ranges from 10 to 60% by weight, more preferably 20 to 50% by weight. The water content of the immobilized enzyme per unit (U) of enzyme preferably ranges from 0.1 to 100 μL/U, more preferably 1 to 50 μL/U.

2. Construction of Reaction System

A mixture of the solvent and prussic acid is saturated with water or an aqueous buffer at a temperature of around the reaction temperature. Since the saturation solubility of water under this condition is about 2% by weight, it is desirable to incorporate water or the aqueous buffer into the reaction system at least in the same amount. On the other hand, the immobilized enzyme should have a high water content enough to ensure its sufficient activity and easy dispersion in the reaction solvent. When water is present in an excess amount, the water content can be adjusted by reducing the amount of water added to the reaction solvent. When the carrier contains slightly less water, the water content can also be adjusted by adding water or the aqueous buffer as such to the reaction system containing the immobilized enzyme.

3. Reaction

In a batch fashion, the immobilized enzyme should be dispersed over the reaction system by stirring or the like. If the immobilized enzyme is filled into a column or the like, the reaction can be carried out by passing a solution containing the substrates through the column at an appropriate flow rate, and then collecting the effluent. In a batch reaction, the product can be collected by stopping the mixing at the time when the reaction is completed, precipitating the immobilized enzyme, and then removing the organic phase containing the product dissolved therein in a general manner. This immobilized enzyme may be re-used by mixing it with a substrate-containing solution prepared in the same manner as the first round.

A carbonyl compound and hydrogen cyanide are used as substrates for the synthesis of an optically active cyanohydrin which can be synthesized according to the first aspect of the present invention.

As used herein, a carbonyl compound means aldehyde or ketone, which is specifically represented by the following formula (I):

$$R^1\text{—CO—}R^2 \qquad (I)$$

wherein
R$^1$ and R$^2$ are different from each other, each of which is a hydrogen atom or a monovalent hydrocarbon group containing at most 22 carbon atoms, in which each of —CH$_2$— and CH$_2$ in —CH$_3$ may be replaced by a carbonyl group, a sulfonyl group, —O— or —S—; =CH$_2$ may be replaced by =O or =S; or each C—H in —CH$_2$—, —CH$_3$, >CH—, =CH— and =CH$_2$ may be replaced by N or a C-halogen group; or R$^1$ and R$^2$ may together form an asymmetric divalent group.

In the above formula (I), a monovalent hydrocarbon group containing at most 22 carbon atoms includes a linear or branched chain hydrocarbon group, a monocyclic hydrocarbon group with or without side chain, a polycyclic hydrocarbon group with or without side chain, a spiro hydrocarbon group with or without side chain, a ring-assembled hydrocarbon group with or without side chain, or a chain hydrocarbon group substituted with the above cyclic hydrocarbon groups. It also includes both saturated and unsaturated hydrocarbon groups, provided that unsaturated hydrocarbon groups having an allene structure (C=C=C) are excluded. A linear or branched chain hydrocarbon group includes, for example, saturated chain hydrocarbon groups such as a linear alkyl group containing at least one carbon atom and a branched alkyl group containing at least 3 carbon atoms; and unsaturated chain hydrocarbon groups such as a linear alkenyl group containing at least 2 carbon atoms, a branched alkenyl group containing at least 3 carbon atoms, a linear alkynyl group containing at least 3 carbon atoms, a branched alkynyl group containing at least 4 carbon atoms, a linear alkadienyl group containing at least 4 carbon atoms and a branched alkadienyl group containing at least 5 carbon atoms. A monocyclic hydrocarbon group includes, for example, saturated monocyclic hydrocarbon groups such as a cycloalkyl group without side chain which contains at least 3 carbon atoms and a cycloalkyl group with side chain which contains at least 4 carbon atoms in total; and unsaturated monocyclic hydrocarbon groups such as a cycloalkenyl group without side chain which contains at least 4 carbon atoms, a cycloalkynyl group with side chain which contains at least 5 carbon atoms in total, a cycloalkadienyl group without side chain which contains at least 5 carbon atoms and a cycloalkadienyl group with side chain which contains at least 6 carbon atoms in total. An unsaturated monocyclic or polycyclic hydrocarbon group includes aromatic hydrocarbon groups such as an aromatic group without side chain which contains 6 to 22 carbon atoms in total, for example, a phenyl group, a 1-naphthyl group, a 2-naphthyl group and a 9-anthryl group; an aromatic group with side chain which contains at least 7 carbon atoms in total; and furthermore ring-assembled hydrocarbon groups such as a phenylphenyl group containing 12 carbon atoms and a phenylphenyl group with side chain which contains at least 13 carbon atoms in total. A polycyclic hydrocarbon group includes a condensed cyclic hydrocarbon group without side chain which contains at least 6 carbon atoms, a condensed cyclic hydrocarbon group with side chain which contains at least 7 carbon atoms in total, a bridged cyclic hydrocarbon group without side chain which contains at least 7 carbon atoms, a bridged cyclic hydrocarbon group with side chain which contains at least 8 carbon atoms in total, a spiro hydrocarbon group without side chain which contains at least 9 carbon atoms in total and a spiro hydrocarbon group with side chain which contains at least 10 carbon atoms in total. In addition, the above condensed cyclic hydrocarbon group without side chain includes those which contain at least 9 carbon atoms in total when one of their condensed rings is a benzene ring, and the above condensed cyclic hydrocarbon group with side chain includes those which contain at least 10 carbon atoms in total when one of their condensed rings is a benzene ring. A ring-assembled hydrocarbon group includes a cycloalkyl-cycloalkyl group without side chain which contains at least 6 carbon atoms in total, a cycloalkyl-cycloalkyl group with side chain which contains at least 7 carbon atoms in total, a cycloalkylidene-cycloalkyl group without side chain which contains at least 6 carbon atoms in total and a cycloalkylidene-cycloalkyl group with side chain which contains at least 7 carbon atoms in total. As used herein, a "cyclic hydrocarbon with side chain" means a cyclic hydrocarbon having a chain hydrocarbon group attached to its ring. Such a chain hydrocarbon group attached to a cyclic hydrocarbon group includes a linear alkyl group which is substituted with an aromatic group without side chain and contains at least 7 carbon atoms in total, a linear alkyl group which is substituted with an aromatic group with side chain and contains at least 8 carbon atoms in total, a branched alkyl group which is substituted with an aromatic group without side chain and contains at least 9 carbon atoms in total, a branched alkyl group which is substituted with an aromatic group with side chain and contains at least 10 carbon atoms in total, a linear alkenyl group which is substituted with an aromatic group without side chain and contains at least 8 carbon atoms in total, a linear alkenyl group which is substituted with an aromatic group with side chain and contains at least 9 carbon atoms in total, a branched alkenyl group which is substituted with an aromatic group without side chain and contains at least 9 carbon atoms in total, a branched alkenyl group which is substituted with an aromatic group with side chain and contains at least 10 carbon atoms in total, a linear alkynyl group which is substituted with an aromatic group without side chain and contains at least 8 carbon atoms in total, a linear alkynyl group which is substituted with an aromatic group with side chain and contains at least 9 carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least 4 carbon atoms in total, a linear alkyl group which is substituted with a cycloalkyl group with side chain and contains at least 5 carbon atoms in total, a branched alkyl group which is substituted with a cycloalkyl group without side chain and contains at least 6 carbon atoms in total, a branched alkyl group which is substituted with a cycloalkyl group with side chain and contains at least 7 carbon atoms in total, a linear alkenyl group which is substituted with a cycloalkyl group without side chain and contains at least 5 carbon atoms in total, a linear alkenyl group which is substituted with a cycloalkyl group with side chain and contains at least 6 carbon atoms in total, a branched alkenyl group which is substituted with a cycloalkyl group without side chain and contains at least 6 carbon atoms in total, a branched alkenyl group which is substituted with a cycloalkyl group with side chain and contains at least 7 carbon atoms in total, a linear alkynyl group which is substituted with a cycloalkyl group without side chain and contains at least 5 carbon atoms in total, a linear alkynyl group which is substituted with a cycloalkyl group with side chain and contains at least 6 carbon atoms in total, a branched alkynyl group which is substituted with a cycloalkyl group without side chain and contains at least 7 carbon atoms in total, a branched alkynyl group which is substituted with a cycloalkyl group with side chain and contains at least 8 carbon atoms in total, a branched alkadienyl group which is substituted with a cycloalkyl group without side chain and contains at least 8 carbon atoms in total, a branched alkadienyl group which is substituted with a cycloalkyl group with side chain and contains at least 9 carbon atoms in total.

Hereinafter, an aromatic group with or without side chain and a phenylphenyl group with or without side chain are collectively referred to as aryl groups, and a linear or branched alkyl group substituted with the aryl group is referred to as an aralkyl group. Other cyclic hydrocarbon groups including both of those having side chain on their ring and those having no side chain are simply referred to as, for example, cycloalkyl groups, unless otherwise specified. Further, chain hydrocarbon groups including both linear and branched ones are also simply referred to as, for example, alkyl groups.

In the above hydrocarbon group, when —$CH_2$— is replaced by a carbonyl group, sulfonyl group, —O— or —S—, a ketone, sulfone, ether or thioether structure is introduced thereinto, respectively. When —$CH_2$— in —$CH_3$ is replaced by a carbonyl group, —O— or —S—, it converts into a formyl (aldehyde) group, a hydroxyl group or a mercapto group, respectively. When a terminal =$CH_2$ is replaced by =O or =S, a ketone or thioketone structure is introduced thereinto, respectively. When C—H in —$CH_2$— is replaced by N, it converts into —NH—. When C—H in >CH— is replaced by N, it converts into >N—. When C—H in =CH— is replaced by N, it converts into =N—. When C—H in a terminal —$CH_3$ is replaced by N, —$NH_2$ is introduced thereinto. When C—H in =$CH_2$ is replaced by N, it converts into =NH. Further, when C—H in —$CH_3$, —$CH_2$—, =CH—, ≡CH or >CH— is replaced by a C-halogen group, that carbon has a halogen atom attached thereto. Furthermore, the replacement by —O—, —S— or N in a carbon chain corresponds to oxa-, thia- or aza-substitution of the hydrocarbon group, respectively. For example, when such a substitution takes place at a ring carbon of the hydrocarbon ring, the hydrocarbon ring converts into a heterocyclic ring containing oxygen, sulfur or nitrogen. The replacement of $CH_2$ and C—H in the hydrocarbon group may independently take place and it may further take place when $CH_2$ or C—H still remains on the carbon after the previous replacement. Furthermore, such a replacement may convert —$CH_2$—$CH_3$ into —CO—O—H (carboxylic structure).

As used herein, a halogen atom refers to a fluorine atom, a chlorine atom, a bromine atom and an iodine atom, with a fluorine atom, a chlorine atom and a bromine atom being preferred.

Accordingly, the above hydrocarbon group may be selected from chain hydrocarbon groups and ring-containing hydrocarbon groups including cyclic hydrocarbon groups, for example, saturated chain hydrocarbon groups such as a linear or branched alkyl group; unsaturated chain hydrocarbon groups such as a linear or branched alkenyl group, a linear or branched alkynyl group and a linear or branched alkadienyl group; saturated cyclic hydrocarbon groups such as a cycloalkyl group; unsaturated cyclic hydrocarbon groups such as a cycloalkenyl group, a cycloalkynyl group and a cycloalkadienyl group; and aromatic hydrocarbon groups such as an aryl group, an aralkyl group and an arylalkenyl group.

In more detail, a linear or branched alkyl group includes a methyl group, an ethyl group, a propyl group, an isopropyl group, a butyl group, a 1-methylpropyl group, a pentyl group, a 1-methylbutyl group, a hexyl group, a 1-methylpentyl group, a heptyl group, a 1-methylhexyl group, a 1-ethylpentyl group, a octyl group, a nonyl group, a decyl group, an undecyl group, a dodecyl group, a tridecyl group, a tetradecyl group, a 2-methylpropyl group, a 2-methylbutyl group, a 3-methylbutyl group, a 2-methylpentyl group, a 3-methylpentyl group, a 4-methylpentyl group, a methylhexyl group, a methylheptyl group, a methyloctyl group, a methylnonyl group, a 1,1-dimethylethyl group, a 1,1-dimethylpropyl group, a 2,6-dimethylheptyl group, a 3,7-dimethyloctyl group and a 2-ethylhexyl group; a cycloalkylalkyl group includes a cyclopentylmethyl group and a cyclohexylmethyl group; a cycloalkyl group includes a cyclopropyl group, a cyclobutyl group, a cyclopentyl group, a methylcyclopentyl group, a cyclohexyl group, a methylcyclohexyl group, a cycloheptyl group and a cyclooctyl group; and a bicycloalkyl group includes a norbornyl group, a bicyclo[2.2.2]octyl group and an adamantyl group. A linear or branched alkenyl group includes a vinyl group, an allyl group, a crotyl (2-butenyl) group and an isopropenyl (1-methylvinyl) group; a cycloalkenyl or cycloalkadienyl group includes a cyclopentenyl group, a cyclopentadienyl group, a cyclohexenyl group and a cyclohexadienyl group. A linear or branched alkynyl group includes an ethynyl group, a propynyl group and a butynyl group. An aryl group includes a phenyl group, a 1-naphthyl group, a 2-naphthyl group, a 2-phenylphenyl group, a 3-phenylphenyl group, a 4-phenylphenyl group, a 9-anthryl group, a methylphenyl group, a dimethylphenyl group, a trimethylphenyl group, an ethylphenyl group, a methylethylphenyl group, a diethylphenyl group, a propylphenyl group and a butylphenyl group. An aralkyl group includes a benzyl group, a 1-naphthylmethyl group, a 2-naphthylmethyl group, a phenethyl (2-phenylethyl) group, a 1-phenylethyl group, a phenylpropyl group, a phenylbutyl group, a phenylpentyl group, a phenylhexyl group, a methylbenzyl group, a methylphenethyl group, a dimethylbenzyl group, a dimethylphenethyl group, a trimethylbenzyl group, an ethylbenzyl group and a diethylbenzyl group. An arylalkenyl group includes a styryl group, a methylstyryl group, an ethylstyryl group, a dimethylstyryl group and a 3-phenyl-2-propenyl group.

The hydrocarbon groups comprising the replacement of $CH_2$ by a carbonyl group, a sulfonyl group, O or S, or comprising the replacement of C—H by N or a C-halogen group include those having one or more structures such as ketone, aldehyde, carboxylic acid, sulfone, ether, thioether, amine, alcohol, thiol, halogen and heterocycles (e.g., oxygen-containing heterocycle, sulfur-containing heterocycle, nitrogen-containing heterocycle). As used herein, an oxygen-containing heterocycle, a sulfur-containing heterocycle and a nitrogen-containing heterocycle mean cyclic hydrocarbon groups whose ring carbon is replaced by oxygen, sulfur and nitrogen, respectively. Further, these heterocycles may contain two or more heteroatoms. Illustrative examples of the hydrocarbon groups comprising the above replacements include those having a ketone structure, such as an acetylmethyl group and an acetylphenyl group; those having a sulfone structure, such as a methanesulfonylmethyl group; those having an ether structure, such as a methoxymethyl group, a methoxyethyl group, an ethoxyethyl group, a methoxypropyl group, a butoxyethyl group, an ethoxyethoxyethyl group, a methoxyphenyl group, a dimethoxyphenyl group and a phenoxymethyl group; those having a thioether structure, such as a methylthiomethyl group and a methylthiophenyl group; those having an amine structure, such as an aminomethyl group, a 2-aminoethyl group, a 2-aminopropyl group, a 3-aminopropyl group, a 2,3-diaminopropyl group, a 2-aminobutyl group, a 3-aminobutyl group, a 4-aminobutyl group, a 2,3-diaminobutyl group, a 2,4-diaminobutyl group, a 3,4-diaminobutyl group, a 2,3,4-triaminobutyl group, a methylaminomethyl group, a dimethylaminomethyl group, a methylaminoethyl group, a propylaminomethyl group, a cyclopentylaminomethyl group, an aminophenyl group, a diaminophenyl group, and an aminomethylphenyl group; those having an oxygen-containing heterocycle, such as a tetrahydrofuranyl group, a tetrahydropyranyl group and a morphorylethyl group; those having an oxygen-containing aromatic heterocycle, such as a furyl group, a furfuryl group, a benzofuryl group and a benzofurfuryl group; those having a sulfur-containing aromatic heterocycle, such as a thienyl group; those having a nitrogen-containing aromatic heterocycle, such as a pyrrolyl group, an imidazolyl group, an oxazolyl group, a thiadiazolyl group, a pyridyl group, a pyrimidinyl group, a pyridazinyl group, a pyrazinyl group, a tetrazinyl group, a quinolyl group, an isoquinolyl group and a pyridylmethyl group; those having an alcohol structure, such as a 2-hydroxyethyl group, a 2-hydroxypropyl group, a 3-hydroxypropyl group, a 2,3-dihydroxypropyl group, a 2-hydroxybutyl group, a 3-hydroxybutyl group, a 4-hydroxybutyl group, a 2,3-dihydroxybutyl group, a 2,4-dihydroxybutyl group, a 3,4-dihydroxybutyl group, a 2,3,4-trihydroxybutyl group, a hydroxyphenyl group, a dihydroxyphenyl group, a hydroxymethylphenyl group and a hydroxyethylphenyl group; those having a thiol structure, such as a 2-mercaptoethyl group, a 2-mercaptopropyl group, a 3-mercaptopropyl group, a 2,3-dimercaptopropyl group, a 2-mercaptobutyl group, a 3-mercaptobutyl group, a 4-mercaptobutyl group and a mercaptophenyl group; those which are halogenated, such as a 2-chloroethyl group, a 2-chloropropyl group, a 3-chloropropyl group, a 2-chlorobutyl group, a 3-chlorobutyl group, a 4-chlorobutyl group, a fluorophenyl group, a chlorophenyl group, a bromophenyl group, a difluorophenyl group, a dichlorophenyl group, a dibromophenyl group, a chlorofluorophenyl group, a trifluorophenyl group, a trichlorophenyl group, a fluoromethylphenyl group and a trifluoromethylphenyl group; those having an amine structure and an alcohol structure, such as a 2-amino-3-hydroxypropyl group, a 3-amino-2-hydroxypropyl group, a 2-amino-3-hydroxybutyl group, a 3-amino-2-hydroxybutyl group, a 2-amino-4-hydroxybutyl group, a 4-amino-2-hydroxybutyl group, a 3-amino-4-hydroxybutyl group, a 4-amino-3-hydroxybutyl group, a 2,4-diamino-3-hydroxybutyl group, a 3-amino-2,4-dihydroxybutyl group, a 2,3-diamino-4-hydroxybutyl group, a 4-amino-2,3-dihydroxybutyl group, a 3,4-diamino-2-hydroxybutyl group, a 2-amino-3,4-dihydroxybutyl group and an aminohydroxyphenyl group; those which are substituted with a halogen atom and a hydroxyl group, such as a fluorohydroxyphenyl group and a chlorohydroxyphenyl group; and those having a carboxylic structure, such as a carboxyphenyl group.

An asymmetric divalent group mentioned under $R^1$ and $R^2$ includes, but is not limited to, norbornan-2-ylidene and 2-norbornen-5-ylidene.

A carbonyl compound of the above formula (I) includes, for example, an aromatic aldehyde such as benzaldehyde, 3-phenoxybenzaldehyde, 4-methylbenzaldehyde, 2-chlorobenzaldehyde, 3-chlorobenzaldehyde, 4-chlorobenzaldehyde, 3-nitrobenzaldehyde, 3,4-methylenedioxybenzaldehyde, 2,3-methylenedioxybenzaldehyde, phenylacetaldehyde and furfural; an aliphatic aldehyde such as acetaldehyde, butylaldehyde, isobutylaldehyde, valeraldehyde and cyclohexanealdehyde; a saturated aliphatic ketone such as ethyl methyl ketone, butyl methyl ketone, methyl propyl ketone, isopropyl methyl ketone, methyl pentyl ketone, methyl (2-methylpropyl) ketone and methyl (3-methylbutyl) ketone; an unsaturated aliphatic ketone such as methyl (2-propenyl) ketone and (3-butenyl) methyl ketone; an alkyl (haloalkyl) ketone such as (3-chloropropyl) methyl ketone; a 2-(protected amino) aldehyde such as 2-(alkoxycarbonylamino)-3-cyclohexylpropionaldehyde; and an alkylthio aliphatic aldehyde such as 3-methylthiopropionaldehyde.

To convert the above aldehyde or ketone into an optically active cyanohydrin, hydrogen cyanide is used as a starting material, which may be supplied in liquid or gaseous form. In addition to hydrogen cyanide, hydrocyanic acid, i.e., prussic acid, which is an aqueous solution of hydrogen cyanide, may also be used in exactly the same manner. Further, any substance which can produce a cyanide ion (CN when added to the reaction system may also be used, including salts of hydrocyanic acid (e.g., sodium cyanide or potassium cyanide) and cyanohydrins (e.g., acetone cyanohydrin).

The preparation of hydroxynitrile lyase enzyme used in the first aspect of the present invention may be carried out by extraction from plant tissues containing the enzyme or by extraction from cultures of recombinant organisms into which a gene of the enzyme has been introduced. The extraction may be accomplished in a general manner. The resultant enzyme preparation may be used without purification unless its components other than hydroxynitrile lyase, if any, affect the enzyme reaction. The hydroxynitrile lyase enzyme thus prepared is immobilized on/in carriers to obtain the immobilized enzyme.

The water content of the immobilized enzyme may be determined from the weight ratio between dried carriers before used for immobilization and the immobilized enzyme prepared. Alternatively, it may also be determined using a Karl Fischer moisture meter or the like.

The amounts of the immobilized enzyme and substrate to be used and a reaction temperature are determined appropriately depending on the type of substrate to be used. In general, the immobilized enzyme may be used in an amount of 1 to 1000 units, preferably 10 to 500 units, relative to 50 mmol of the carbonyl compound as a substrate. The substrate concentration may be generally set between 0.1 and 10 mol/L when the carbonyl compound is used. Hydrogen cyanide may be added at a concentration of 1- to 5-fold molar excess, preferably 1.1- to 3-fold molar excess, relative to the carbonyl compound. Since the enzyme activity and reaction rate in this reaction will vary depending on the substrate concentration, the substrate concentration should be determined appropriately according to the type of carbonyl compound to be used. The reaction is preferably, but not always, continued until the conversion ratio of carbonyl compound reaches 80% or more, preferably 90% or more. The reaction may be carried out at any temperature at which the enzyme sufficiently catalyzes the reaction, generally at 0 to 40° C., preferably at 4 to 30° C.

The product produced in the first aspect of the present invention, such as an optically active cyanohydrin, may be measured and assayed by, for example, high performance liquid chromatography (HPLC) and, if necessary, may be separated and purified by a standard procedure such as extraction, distillation under reduced pressure, or column separation. When the product is to be stored for a long time, a stabilizing agent may be added thereto.

Any enzyme reaction which uses an aldehyde compound as a substrate may be used in the second aspect of the present invention. A preferred enzyme reaction uses both hydrogen cyanide and an aldehyde compound as substrates.

In addition, any enzyme may be used in the second aspect of the present invention without particular limitations, so long as it can be used for the above enzyme reaction. Hydroxynitrile lyase may be preferably used, which catalyzes the synthesis of an optically active cyanohydrin from an aldehyde compound and hydrogen cyanide.

As used herein, a "reaction inhibitor" means a substance that inhibits the enzyme reaction so as to decrease its reaction rate and/or so as to reduce the yield of a target product. In the above enzyme reaction using an aldehyde compound as a substrate, the reaction inhibitor includes, for example, a carboxylic acid compound corresponding to the aldehyde compound.

In the second aspect, the present invention uses hydroxynitrile lyase as described in connection with the first aspect.

Any aldehyde compound may be used in the present invention without particular limitations. A preferred aldehyde compound can provide phase separation when mixed with water.

Specifically, it has the following formula (II):

wherein
R is a monovalent hydrocarbon group containing at most 22 carbon atoms, in which each $CH_2$ in $-CH_2-$ and $-CH_3$ may be replaced by a carbonyl group, a sulfonyl group, $-O-$ or $-S-$; $=CH_2$ may be replaced by $=O$ or $=S$; or each C—H in $-CH_2-$, $-CH_3$, $>CH-$, $=CH-$ and $=CH_2$ may be replaced by N or a C-halogen group.

In the above formula (II), a monovalent hydrocarbon group containing at most 22 carbon atoms includes a linear or branched chain hydrocarbon group, a monocyclic hydrocarbon group with or without side chain, a polycyclic hydrocarbon group with or without side chain, a spiro hydrocarbon group with or without side chain, a ring-assembled hydrocarbon group with or without side chain, or a chain hydrocarbon group substituted with the above cyclic hydrocarbon groups. It also includes both saturated and unsaturated hydrocarbon groups, provided that unsaturated hydrocarbon groups having an allene structure (C=C=C) are excluded. A linear or branched chain hydrocarbon group includes, for example, saturated chain hydrocarbon groups such as a linear alkyl group containing at least 2 carbon atoms and a branched alkyl group containing at least 3 carbon atoms; and unsaturated chain hydrocarbon groups such as a linear alkenyl group containing at least 2 carbon atoms, a branched alkenyl group containing at least 3 carbon atoms, a linear alkynyl group containing at least 3 carbon atoms, a branched alkynyl group containing at least 4 carbon atoms, a linear alkadienyl group containing at least 4 carbon atoms and a branched alkadienyl group containing at least 5 carbon atoms. A monocyclic hydrocarbon group includes, for example, saturated monocyclic hydrocarbon groups such as a cycloalkyl group without side chain which contains at least 3 carbon atoms and a cycloalkyl group with side chain which contains at least 4 carbon atoms in total; and unsaturated monocyclic hydrocarbon groups such as a cycloalkenyl group without side chain which contains at least 4 carbon atoms, a cycloalkynyl group with side chain which contains at least 5 carbon atoms in total, a cycloalkadienyl group without side chain which contains at least 5 carbon atoms and a cycloalkadienyl group with side chain which contains at least 6 carbon atoms in total. An unsaturated monocyclic or polycyclic hydrocarbon group includes aromatic hydrocarbon groups such as an aromatic group without side chain which contains 6 to 22 carbon atoms in total, for example, a phenyl group, a 1-naphthyl group, a 2-naphthyl group and a 9-anthryl group; an aromatic group with side chain which contains at least 7 carbon atoms in total; and furthermore ring-assembled hydrocarbon groups such as a phenylphenyl group containing 12 carbon atoms and a phenylphenyl group with side chain which contains at least 13 carbon atoms in total. A polycyclic hydrocarbon group includes a condensed cyclic hydrocarbon group without side chain which contains at least 6 carbon atoms, a condensed cyclic hydrocarbon group with side chain which contains at least 7 carbon atoms in total, a bridged cyclic hydrocarbon group without side chain which contains at least 7 carbon atoms, a bridged cyclic hydrocarbon group with side chain which contains at least 8 carbon atoms in total, a spiro hydrocarbon group without side chain which contains at least 9 carbon atoms in total and a spiro hydrocarbon group with side chain which contains at least 10 carbon atoms in total. In addition, the above condensed cyclic hydrocarbon group without side chain includes those which contain at least 9 carbon atoms in total when one of their condensed rings is a benzene ring, and the above condensed cyclic hydrocarbon group with side chain includes those which contain at least 10 carbon atoms in total when one of their condensed rings is a benzene ring. A ring-assembled hydrocarbon group includes a cycloalkyl-cycloalkyl group without side chain which contains at least 6 carbon atoms in total, a cycloalkyl-cycloalkyl group with side chain which contains at least 7 carbon a toms in total, a cycloalkylidene-cycloalkyl group without side chain which contains at least 6 carbon atoms in total and a cycloalkylidene-cycloalkyl group with side chain which contains at least 7 carbon atoms in total. As used herein, a "cyclic hydrocarbon with side chain" means a cyclic hydrocarbon having a chain hydrocarbon group attached to its ring. Such a chain hydrocarbon group attached to a cyclic hydrocarbon group includes a linear alkyl group which is substituted with an aromatic group with out side chain and contains at least 7 carbon atoms in total, a linear alkyl group which is substituted with an aromatic group with side chain and contains at least 8 carbon atoms in total, a branched alkyl group which is substituted with an aromatic group without side chain and contains at least 9 carbon atoms in total, a branched alkyl group which is substituted with an aromatic group with side chain and contains at least 10 carbon atoms in total, a linear alkenyl group which is substituted with an aromatic group without side chain and contains at least 8 carbon atoms in total, a linear alkenyl group which is substituted with an aromatic group with side chain and contains at least 9 carbon atoms in total, a branched alkenyl group which is substituted with an aromatic group without side chain and contains at least 9 carbon atoms in total, a branched alkenyl group which is substituted with an aromatic group with side chain and contains at least 10 carbon atoms in total, a linear alkynyl group which is substituted with an aromatic group without side chain and contains at least 8 carbon atoms in total, a linear alkynyl group which is substituted with an aromatic group with side chain and contains at least 9 carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least 4 carbon atoms in total, a linear alkyl group which is substituted with a cycloalkyl group with side chain and contains at least 5 carbon atoms in total, a branched alkyl group which is substituted with a cycloalkyl group without side chain and contains at least 6 carbon atoms in total, a branched alkyl group which is substituted with a cycloalkyl group with side chain and contains at least 7 carbon atoms in total, a linear alkenyl group which is substituted with a cycloalkyl group without side chain and contains at least 5 carbon atoms in total, a linear alkenyl group which is substituted with a cycloalkyl group with side chain and contains at least 6 carbon atoms in total, a branched alkenyl group which is substituted with a cycloalkyl group without side chain and contains at least 6 carbon atoms in total, a branched alkenyl group which is substituted with a cycloalkyl group with side chain and contains at least 7 carbon atoms in total, a linear alkynyl group which is substituted with a cycloalkyl group without side chain and contains at least 5 carbon atoms in total, a linear alkynyl group which is substituted with a cycloalkyl group with side chain and contains at least 6 carbon atoms in total, a branched alkynyl group which is substituted with a cycloalkyl group without side chain and contains at least 7 carbon atoms in total, a branched alkynyl group which is substituted with a cycloalkyl group with side chain and contains at least 8 carbon atoms in total, a branched alkadienyl group which is substituted with a cycloalkyl group without side chain and contains at least 8 carbon atoms in total, a branched alkadienyl group which is substituted with a cycloalkyl group with side chain and contains at least 9 carbon atoms in total.

Hereinafter, an aromatic group with or without side chain and a phenylphenyl group with or without side chain are collectively referred to as aryl groups, and a linear or branched alkyl group substituted with the aryl group is referred to as an aralkyl group. Other cyclic hydrocarbon groups including both of those having side chain on their ring and those having no side chain are simply referred to as, for example, cycloalkyl groups, unless otherwise specified. Further, chain hydrocarbon groups including both linear and branched ones are also simply referred to as, for example, alkyl groups.

In the above hydrocarbon group, when —CH$_2$— is replaced by a carbonyl group, sulfonyl group, —O— or —S—, a ketone, sulfone, ether or thioether structure is introduced thereinto, respectively. When —CH$_2$— in —CH$_3$ is replaced by a carbonyl group, —O— or —S—, it converts into a formyl (aldehyde) group, a hydroxyl group or a mercapto group, respectively. When a terminal =CH$_2$ is replaced by =O or =S, a ketone or thioketone structure is introduced thereinto, respectively. When C—H in —CH$_2$— is replaced by N, it converts into —NH—. When C—H in >CH— is replaced by N, it converts into >N—. When C—H in =CH— is replaced by N, it converts into =N—. When C—H in a terminal —CH$_3$ is replaced by N, —NH$_2$ is introduced thereinto. When C—H in =CH$_2$ is replaced by N, it converts into =NH. Further, when C—H in —CH$_3$, —CH$_2$—, =CH—, ≡CH or >CH— is replaced by a C-halogen bond, that carbon has a halogen atom attached thereto. Furthermore, the replacement by —O—, —S— or N in a carbon chain corresponds to oxa-, thia- or aza-substitution of the hydrocarbon group, respectively. For example, when such a substitution takes place at a ring carbon of the hydrocarbon ring, the hydrocarbon ring converts into a heterocyclic ring containing oxygen, sulfur or nitrogen. The replacement of CH$_2$ and C—H in the hydrocarbon group may independently take place and it may further take place when CH$_2$ or C—H still remains on the carbon after the previous replacement.

As used herein, a halogen atom refers to a fluorine atom, a chlorine atom, a bromine atom and an iodine atom, with a fluorine atom, a chlorine atom and a bromine atom being preferred.

Accordingly, the above hydrocarbon group may be selected from chain hydrocarbon groups and ring-containing hydrocarbon groups including cyclic hydrocarbon groups, for example, saturated chain hydrocarbon groups such as a linear or branched alkyl group; unsaturated chain hydrocarbon groups such as a linear or branched alkenyl group, a linear or branched alkynyl group and a linear or branched alkadienyl group; saturated cyclic hydrocarbon groups such as a cycloalkyl group; unsaturated cyclic hydrocarbon groups such as a cycloalkenyl group, a cycloalkynyl group and a cycloalkadienyl group; and aromatic hydrocarbon groups such as an aryl group, an aralkyl group and an arylalkenyl group.

In more detail, a linear or branched alkyl group includes an ethyl group, a propyl group, an isopropyl group, a butyl group, a 1-methylpropyl group, a pentyl group, a 1-methylbutyl group, a hexyl group, a 1-methylpentyl group, a heptyl group, a 1-methylhexyl group, a 1-ethylpentyl group, a octyl group, a nonyl group, a decyl group, an undecyl group, a dodecyl group, a tridecyl group, a tetradecyl group, a 2-methylpropyl group, a 2-methylbutyl group, a 3-methylbutyl group, a 2-methylpentyl group, a 3-methylpentyl group, a 4-methylpentyl group, a methylhexyl group, a methylheptyl group, a methyloctyl group, a methylnonyl group, a 1,1-dimethylethyl group, a 1,1-dimethylpropyl group, a 2,6-dimethylheptyl group, a 3,7-dimethyloctyl group and a 2-ethylhexyl group; a cycloalkylalkyl group includes a cyclopentylmethyl group and a cyclohexylmethyl group; a cycloalkyl group includes a cyclopropyl group, a cyclobutyl group, a cyclopentyl group, a methylcyclopentyl group, a cyclohexyl group, a methylcyclohexyl group, a cycloheptyl group and a cyclooctyl group; and a bicycloalkyl group includes a norbornyl group, a bicyclo [2.2.2] octyl group and an adamantyl group. A linear or branched alkenyl group includes a vinyl group, an allyl group, a crotyl (2-butenyl) group and an isopropenyl (1-methylvinyl) group; a cycloalkenyl or cycloalkadienyl group includes a cyclopentenyl group, a cyclopentadienyl group, a cyclohexenyl group and a cyclohexadienyl group. A linear or branched alkynyl group includes an ethynyl group, a propynyl group and a butynyl group. An aryl group includes a phenyl group, a 1-naphthyl group, a 2-naphthyl group, a 2-phenylphenyl group, a 3-phenylphenyl group, a 4-phenylphenyl group, a 9-anthryl group, a methylphenyl group, a dimethylphenyl group, a trimethylphenyl group, an ethylphenyl group, a methylethylphenyl group, a diethylphenyl group, a propylphenyl group and a butylphenyl group. An aralkyl group includes a benzyl group, a 1-naphthylmethyl group, a 2-naphthylmethyl group, a phenethyl (2-phenylethyl) group, a 1-phenylethyl group, a phenylpropyl group, a phenylbutyl group, a phenylpentyl group, a phenylhexyl group, a methylbenzyl group, a methylphenethyl group, a dimethylbenzyl group, a dimethylphenethyl group, a trimethylbenzyl group, an ethylbenzyl group and a diethylbenzyl group. An arylalkenyl group includes a styryl group, a methylstyryl group, an ethylstyryl group, a dimethylstyryl group and a 3-phenyl-2-propenyl group.

The hydrocarbon groups comprising the replacement of $CH_2$ by a carbonyl group, a sulfonyl group, O or S, or comprising the replacement of C—H by N or a C-halogen group include those having one or more structures such as ketone, aldehyde, sulfone, ether, thioether, amine, alcohol, thiol, halogen and heterocycles (e.g., oxygen-containing heterocycle, sulfur-containing heterocycle, nitrogen-containing heterocycle). As used herein, an oxygen-containing heterocycle, a sulfur-containing heterocycle and a nitrogen-containing heterocycle mean cyclic hydrocarbon groups whose ring carbon is replaced by oxygen, sulfur and nitrogen, respectively. Further, these heterocycles may contain two or more heteroatoms. Illustrative examples of the hydrocarbon groups comprising the above replacements include those having a ketone structure, such as an acetylmethyl group and an acetylphenyl group; those having a sulfone structure, such as a methanesulfonylmethyl group; those having an ether structure, such as a methoxymethyl group, a methoxyethyl group, an ethoxyethyl group, a methoxypropyl group, a butoxyethyl group, an ethoxyethoxyethyl group, a methoxyphenyl group, a dimethoxyphenyl group and a phenoxymethyl group; those having a thioether structure, such as a methylthiomethyl group and a methylthiophenyl group; those having an amine structure, such as a 2-aminopropyl group, a 3-aminopropyl group, a 2,3-diaminopropyl group, a 2-aminobutyl group, a 3-aminobutyl group, a 4-aminobutyl group, a 2,3-diaminobutyl group, a 2,4-diaminobutyl group, a 3,4-diaminobutyl group, a 2,3,4-triaminobutyl group, a methylaminomethyl group, a dimethylaminomethyl group, a methylaminoethyl group, a propylaminomethyl group, a cyclopentylaminomethyl group, an aminophenyl group, a diaminophenyl group, and an aminomethylphenyl group; those having an oxygen-containing heterocycle, such as a tetrahydrofuranyl group, a tetrahydropyranyl group and a morphorylethyl group; those having an oxygen-containing aromatic heterocycle, such as a furyl group, a furfuryl group, a benzofuryl group and a benzofurfuryl group; those having a sulfur-containing aromatic heterocycle, such as a thienyl group; those having a nitrogen-containing aromatic heterocycle, such as a pyrrolyl group, an imidazolyl group, an oxazolyl group, a thiadiazolyl group, a pyridyl group, a pyrimidinyl group, a pyridazinyl group, a pyrazinyl group, a tetrazinyl group, a quinolyl group, an isoquinolyl group and a pyridylmethyl group; those having an alcohol structure, such as a 2-hydroxypropyl group, a 3-hydroxypropyl group, a 2,3-dihydroxypropyl group, a 2-hydroxybutyl group, a 3-hydroxybutyl group, a 4-hydroxybutyl group, a 2,3-dihydroxybutyl group, a 2,4-dihydroxybutyl group, a 3,4-dihydroxybutyl group, a 2,3,4-trihydroxybutyl group, a hydroxyphenyl group, a dihydroxyphenyl group, a hydroxymethylphenyl group and a hydroxyethylphenyl group; those having a thiol structure, such as a 2-mercaptoethyl group, a 2-mercaptopropyl group, a 3-mercaptopropyl group, a 2,3-dimercaptopropyl group, a 2-mercaptobutyl group, a 3-mercaptobutyl group, a 4-mercaptobutyl group and a mercaptophenyl group; those which are halogenated, such as a 2-chloroethyl group, a 2-chloropropyl group, a 3-chloropropyl group, a 2-chlorobutyl group, a 3-chlorobutyl group, a 4-chlorobutyl group, a fluorophenyl group, a chlorophenyl group, a bromophenyl group, a difluorophenyl group, a dichlorophenyl group, a dibromophenyl group, a chlorofluorophenyl group, a trifluorophenyl group, a trichlorophenyl group, a fluoromethylphenyl group and a trifluoromethylphenyl group; those having an amine structure and an alcohol structure, such as a 2-amino-3-hydroxypropyl group, a 3-amino-2-hydroxypropyl group, a 2-amino-3-hydroxybutyl group, a 3-amino-2-hydroxybutyl group, a 2-amino-4-hydroxybutyl group, a 4-amino-2-hydroxybutyl group, a 3-amino-4-hydroxybutyl group, a 4-amino-3-hydroxybutyl group, a 2,4-diamino-3-hydroxybutyl group, a 3-amino-2,4-dihydroxybutyl group, a 2,3-diamino-4-hydroxybutyl group, a 4-amino-2,3-dihydroxybutyl group, a 3,4-diamino-2-hydroxybutyl group, a 2-amino-3,4-dihydroxybutyl group and an aminohydroxyphenyl group; and those which are substituted with a halogen atom and a hydroxyl group, such as a fluorohydroxyphenyl group and a chlorohydroxyphenyl group.

An aldehyde compound of the above formula (II) includes, for example, an aromatic aldehyde such as benzaldehyde, 3-phenoxybenzaldehyde, 4-methylbenzaldehyde, 2-chlorobenzaldehyde, 3-chlorobenzaldehyde, 4-chlorobenzaldehyde, 3-nitrobenzaldehyde, 3,4-methylenedioxybenzaldehyde, 2,3-methylenedioxybenzaldehyde, phenylacetaldehyde and furfural; an aliphatic aldehyde such as butylaldehyde, isobutylaldehyde, valeraldehyde and cyclohexanealdehyde; a 2-(protected amino) aldehyde such as 2-(alkoxycarbonylamino)-3-cyclohexylpropionaldehyde; and an alkylthio aliphatic aldehyde such as 3-methylthiopropionaldehyde.

To convert the above aldehyde compound into an optically active cyanohydrin, hydrogen cyanide is used as a starting material, which may be supplied in liquid or gaseous form in a general manner. In addition to hydrogen cyanide, hydrocyanic acid, which is an aqueous solution of hydrogen cyanide (i.e., aqueous hydrogen cyanide), may also be used in exactly the same manner. Further, any substance which can produce a cyanide ion ($CN^-$) when added to the reaction system may also be used, including salts of hydrocyanic acid (e.g., sodium cyanide or potassium cyanide) or cyanohydrins (e.g., acetone cyanohydrin).

In the second aspect of the present invention, there is no particular limitation on the purity of the aldehyde compound to be used as a starting material. An aldehyde compound containing a carboxylic acid compound may be preferably used in the second aspect of the present invention because it inhibits enzyme activity when used as such for the enzyme reaction. In particular, in a case where the enzyme reaction uses a starting aldehyde compound at a high concentration of 1 M or more, it is desirable to apply the second aspect of the present invention to the enzyme reaction because such a concentrated aldehyde compound containing at least 0.1 wt % of a carboxylic acid compound causes a significant inhibition of the enzyme reaction.

As used herein, an alkaline treatment means a procedure which comprises mixing the aldehyde compound with an alkaline aqueous solution and then separating the aqueous phase from the aldehyde phase in a general manner. The aldehyde compound thus alkaline-treated may be used for the enzyme reaction with or without further general purification.

Any alkali which can give an alkaline aqueous solution when dissolved in water may be used for the alkaline treatment in the second aspect of the present invention. Illustrative examples include, but are not limited to, inorganic base compounds such as sodium hydroxide, potassium hydroxide, calcium hydroxide or ammonia and organic base compounds such as amino compounds.

There is no particular limitation on the concentration of the alkaline aqueous solution, but it preferably ranges from 0.001 N to 10 N, more preferably about 0.01 N to 5 N. Alternatively, the concentration of the alkaline aqueous solution may vary widely as long as the alkaline-treated aldehyde compound, when added as is, to the enzyme reaction mixture, does not provide a pH at which there would be a loss of enzyme activity.

The amount of the alkaline aqueous solution to be added may be an amount which permits phase separation between aqueous and aldehyde phases when the alkaline aqueous solution is mixed with the aldehyde compound, or may be determined appropriately depending on the content of a reaction inhibitor such as a carboxylic acid compound present in the aldehyde compound. Further, the alkaline treatment may be carried out once or plural times until a reaction inhibitor such as a carboxylic acid compound reaches a desired concentration or below.

The above alkaline-treated aldehyde compound is almost free from reaction inhibitors. Among reaction inhibitors, in particular, a carboxylic acid compound corresponding to the aldehyde compound can be almost completely removed, thereby resulting in a content reduced to 0.1 wt % or less, preferably 0.05 wt % or less. Such an alkaline-treated aldehyde compound may be used for the enzyme reaction in which an aldehyde compound is used as a substrate.

The above alkaline treatment given to a starting aldehyde compound achieves effective removal of reaction inhibitors contained in the aldehyde compound, in particular, a carboxylic acid compound corresponding to the aldehyde compound. Hence, the use of such an alkaline-treated aldehyde compound can prevent the enzyme reaction from being inhibited by reaction inhibitors such as the above carboxylic acid compound, resulting in a significantly improved yield of a target product.

In the third aspect, the present invention uses hydroxynitrile lyase as described in connection with the first aspect.

In the third aspect of the present invention, the above enzyme may be used in any form such as powder, liquid, or immobilized form on/in a suitable carrier. Various carriers may be used for immobilizing the enzyme, for example, a porous inorganic carrier, a fibrous carrier such as cellulose, or a carrier made of a polymer compound(s). Specific examples include, but are not limited to, porous ceramic particles, porous silica gel particles, zeolite particles, natural polymer gels such as agar, calcium alginate and chitosan, and synthetic polymer gels such as polyacrylic acid, polyacrylamide and polyvinyl alcohol. Enzyme molecules may be immobilized in any manner, for example, by allowing carriers to absorb an enzyme solution, by mixing carriers with an enzyme solution to immobilize enzyme molecules on/in the carriers by absorption, by entrapping and immobilizing enzyme molecules within carriers, or by cross-linking enzyme molecules via crosslinkers.

In the third aspect of the present invention, a carbonyl compound and prussic acid (hydrocyanic acid) are used as starting materials for the production of an optically active cyanohydrin.

As used herein, a carbonyl compound means aldehyde or ketone, for example, those are specifically represented by formula (1) mentioned above.

Prussic acid containing an acidic substance as a stabilizer is used in the third aspect of the present invention. As used herein, a stabilizer means an acidic substance, such as sulfurous acid and sulfuric acid, which is added to prussic acid produced in bulk in order to prevent prussic acid from being denatured by polymerization etc. and in order to stabilize product quality.

Prussic acid used in the third aspect of the present invention, which contains an acidic substance as a stabilizer, means prussic acid that provides an aqueous phase with pH 5 or less when dissolved at a concentration of 1.5 M in an organic solvent substantially immiscible with water, mixed with pure water at such a ratio that the mixture separates into organic and aqueous phases, and then allowed to stand. Preferably, prussic acid which provides an aqueous phase with pH 4 or less is applied in the method of the third aspect of the present invention.

In the third aspect of the present invention, the inhibitory effect on an enzyme caused by the stabilizer contained in prussic acid may be reduced, for example, by dissolving prussic acid containing an acidic substance as a stabilizer in an organic solvent substantially immiscible with water to give an organic solution of prussic acid, adding a buffer to this solution in a saturation amount or more, mixing, and then collecting the organic phase, which is used for the reaction; or by adjusting that prussic acid between pH 5 and pH 6 by addition of an alkaline aqueous solution or an aqueous buffer having buffering ability in a range of pH 4 to pH 7.

By way of example, a procedure for reducing the above stabilizer's inhibitory effect on an enzyme will be presented below.

1. Dissolve a given amount of prussic acid containing the stabilizer into an organic solvent substantially immiscible with water (optionally pre-saturated with water or an aqueous buffer).
2. Add a buffer in an excess amount greater than the amount soluble in the above solution, mix and allow to stand.
3. Collect the organic phase separated from the aqueous phase. Use in the reaction.

Such a very simple procedure as mentioned above achieves effective removal of an adverse effect caused by the stabilizer contained in an industrially produced prussic acid.

Hydrogen cyanide may be supplied in liquid or gaseous form.

A buffer used in the procedure for reducing the stabilizer's inhibitory effect on an enzyme means a buffer exhibiting buffering ability around the optimum pH for enzyme activity. Specific examples include citrate, glutarate, malate, malonate, o-phthalate and succinate buffers. In general, a buffer having a pH of 4 to 7, preferably 5 to 7, is used. The buffer preferably has a concentration sufficient to keep the aqueous phase at pH 5 to pH 7 after mixing with the organic solvent containing a given amount of prussic acid dissolved therein.

In the third aspect of the present invention, an organic solvent substantially immiscible with water is used as a reaction solvent in order to improve the concentration of starting materials and productivity. As used herein, an "organic solvent substantially immiscible with water" means an organic solvent except for those soluble in water in any proportion. Any solvent may be used as an organic solvent without particular limitations, so long as it is substantially immiscible with water, enables a substrate and a product to be sufficiently dissolved therein and has no influence upon an enzyme reaction. Such a solvent may be selected appropriately according to the nature of aldehyde or ketone to be used as a starting material for the synthesis, and the nature of cyanohydrin obtainable as a reaction product.

Specific examples of an organic solvent substantially immiscible with water include optionally halogenated hydrocarbon solvents such as saturated or unsaturated linear, branched or cyclic aliphatic hydrocarbons and aromatic hydrocarbons, for example, pentane, hexane, cyclohexane, benzene, toluene, xylene, methylene chloride and chloroform; optionally halogenated alcoholic solvents such as saturated or unsaturated linear, branched or cyclic aliphatic alcohols and aralkyl alcohols, for example, n-butanol, isobutanol, t-butanol, hexanol, cyclohexanol and n-amyl alcohol; optionally halogenated ether solvents such as saturated or unsaturated linear, branched or cyclic aliphatic ethers and aromatic ethers, for example, diethyl ether, dipropyl ether, diisopropyl ether, dibutyl ether, t-butyl methyl ether and dimethoxyethane; and optionally halogenated ester solvents such as saturated or unsaturated linear, branched or cyclic aliphatic esters and aromatic esters, for example, methyl formate, methyl acetate, ethyl acetate, butyl acetate and methyl propionate. These solvents may be used alone or in combination.

The organic solvent mentioned above may be saturated with water or an aqueous buffer. Alternatively, water or an aqueous buffer may be added in an excess amount to the organic solvent to give a two-phase system comprising organic and aqueous phases. The saturation of the organic solvent with water or an aqueous buffer may be accomplished in any manner, for example, by mixing the organic solvent with water or an aqueous buffer at such a ratio that the mixture separates into two phases, followed by stirring for a while and allowing to stand, to collect the organic phase, which is then used for the reaction. Any aqueous buffer may be used here, including the buffers mentioned above.

In a case where an industrially produced prussic acid containing a stabilizer is used for the synthesis of an optically active cyanohydrin, the third aspect of the present invention provides a method for reducing an adverse effect on an enzyme caused by the stabilizer contained in that prussic acid. The method of the present invention does not depend on the intended form of prussic acid. That is, prussic acid subjected to the method of the third aspect of the present invention to reduce an adverse effect of the stabilizer may be effectively used in any reaction system, including a mixed system comprising water and an organic solvent, an organic solvent system, a two-phase system comprising water and an organic solvent, and a system using an immobilized enzyme.

The amounts of the immobilized enzyme and substrate to be used and a reaction temperature are determined appropriately depending on the type of substrate to be used. In general, the immobilized enzyme may be used in an amount of 1 to 1000 units, preferably 10 to 500 units, relative to 50 mmol of the carbonyl compound as a substrate. The substrate concentration may be generally set between 0.1 and 10 mol/L when the carbonyl compound is used. Hydrogen cyanide may be added at a concentration of 1- to 5-fold molar excess, preferably 1.1- to 3-fold molar excess, relative to the carbonyl compound. Since the enzyme activity and reaction rate in this reaction will vary depending on the substrate concentration, the substrate concentration should be determined appropriately according to the type of carbonyl compound to be used. The reaction is preferably, but not always, continued until the conversion ratio of carbonyl compound reaches 80% or more, preferably 90% or more. The reaction may be carried out at any temperature at which the enzyme sufficiently catalyzes the reaction, generally at 0 to 40° C., preferably at 4 to 30° C.

The optically active cyanohydrin produced in the third aspect of the present invention may be measured and assayed by, for example, high performance liquid chromatography (HPLC) and, if necessary, may be separated and purified by a standard procedure such as extraction, distillation under reduced pressure, or column separation. When the product is to be stored for a long time, a stabilizing agent may be added thereto.

In the fourth aspect of the present invention, a reaction solvent and unreacted prussic acid may be collected by distillation from a reaction solution containing an optically active cyanohydrin after completion of an enzyme reaction. The fourth aspect of the present invention can be applied in a case where a reaction solvent has a lower boiling point than that of the cyanohydrin. The distillation is preferably carried out at a relatively low temperature and under reduced pressure, rather than at an elevated temperature and under normal pressure, because an optically active cyanohydrin is unstable at an elevated temperature.

Reduced pressure and temperature to be applied may be determined appropriately according to the type of organic solvent to be used. Generally, in a case where a solvent to be used has a boiling point of about 30 to 100° C., such as t-butyl methyl ether or diisopropyl ether, distillation temperature and reduced pressure may be preferably, but not always, set at 20 to 70° C., more preferably 20 to 60° C., and at 1 to 600 torr, preferably 5 to 400 torr, respectively. The distilled solvent and prussic acid may be effectively collected, for example, by using a condenser cooled to 10° C. or below. In this process, water contained in a reaction solution may also be azeotroped therefrom. To recycle a reaction solvent and prussic acid, the aqueous phase is separated off after the above distillation process and the organic phase is collected for use in the next reaction. The collected organic phase contains the greater part of prussic acid contained in a reaction mixture.

In this distillation process, a stabilizer for an optically active cyanohydrin may be added to a reaction solution containing an optically active cyanohydrin collected after completion of an enzyme reaction. Any stabilizer capable of keeping the above reaction solution at an acidic pH may be used. For example, an organic acid (e.g., p-toluenesulfonic acid and acetic acid) or an inorganic acid (e.g., sulfuric acid) may be added in an amount of $1/200$ to $1/10$ mol per mol of cyanohydrin.

The collected organic solvent containing unreacted prussic acid may then be used as a solvent for the next enzyme reaction.

The first to fourth aspects of the present invention may be performed in combination, if necessary.

According to the first aspect, the present invention can provide highly efficient and stable synthesis of a target product.

According to the second aspect of the present invention, even an aldehyde altered to the extent that it affects enzyme activity when used in an enzyme reaction can be almost completely freed from reaction inhibitors present in the aldehyde by means of a very simple alkaline treatment. Such an alkaline-treated aldehyde can be used in an enzyme reaction as a starting material equivalent to an unaltered aldehyde, resulting in a significantly improved yield of a target product.

According to the third aspect, the present invention can prevent an enzyme (e.g., hydroxynitrile lyase) from losing its activity and can provide a significantly extended life-time for the enzyme. Accordingly, the present invention achieves industrially stable and low-cost production of an optically active cyanohydrin using an industrially produced prussic acid containing a stabilizer.

According to the fourth aspect, the present invention achieves recycling of a reaction solvent and unreacted prussic acid in a method for producing an optically active cyanohydrin.

This specification includes part or all of the contents as disclosed in the specifications of Japanese Patent Applications Nos. 2000-166578, 2000-166579 and 2000-206130, which are the bases of the priority claim of the present application.

BRIEF DESCRIPTION OF THE DRAWINGS

FIG. 4 shows the relationships between the number of reaction batches and the conversion ratio of aldehyde and the enantiomer excess. Reference signs found in FIG. 4 have the following meanings:
- ● Conversion ratio of aldehyde
- ▲ Enantiomer excess

DETAILED DESCRIPTION OF THE PREFERRED EMBODIMENTS

Figure 1:
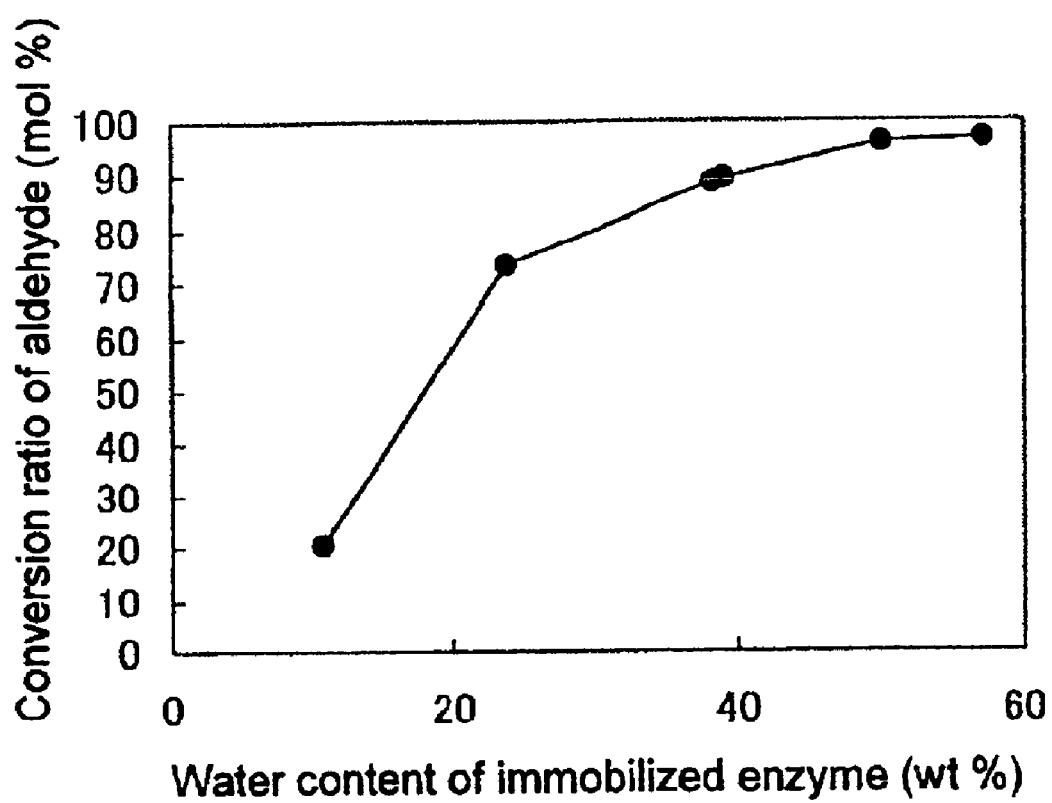
FIG. 1 shows the relationship between water content and reaction efficiency of the immobilized enzyme.

The present invention will be further described in the following examples. The examples are provided for illustrative purposes only, and are not intended to limit the scope of the invention.

PREPARATION EXAMPLE 1

Preparation of (R)-hydroxynitrile Lyase (1) 100 g of ground almond (*Prunus amygdalus*) seeds was mixed and stirred with 200 ml acetone for 2 hours, and then filtrated to collect the solids. After drying, the solids were mixed with 600 g of water and adjusted to pH 7.5 with aqueous ammonia, followed by overnight mixing with stirring. Subsequently, the resulting slurry was centrifuged to collect the supernatant, which was then adjusted to pH 5.5 and centrifuged to give a solution free from insoluble components.

(2) The (R)-hydroxynitrile lyase enzyme solution prepared in (1) above was assayed for its activity. The production rate of benzaldehyde decomposed from DL-mandelonitrile (substrate) by the action of the enzyme was measured as a change in absorbance at 249.6 nm to calculate enzyme activity. An enzyme activity at which 1 μmol of benzaldehyde is produced per minute is defined as 1 unit (U). The enzyme solution prepared in (1) above was assayed in this manner, indicating that 25,000 units of enzyme having an activity of 60.57 U/ml can be collected.

PREPARATION EXAMPLE 2

Preparation of (S)-hydroxynitrile Lyase (1) (S)-hydroxynitrile lyase was prepared using yeast, *Saccharomyces cerevisiae*, as a host by introducing the (S)-hydroxynitrile lyase gene cloned from *Manihot esculenta* into the yeast and then culturing the resulting recombinant yeast. The recombinant yeast was cultured in 1 L of YPD medium containing 1% yeast extract, 2% peptone and 2% glucose for 24 hours to collect the yeast cells, which were then homogenized and purified to give a solution free from insoluble components.

(2) The (S)-hydroxynitrile lyase enzyme solution prepared in (1) above was assayed in the same manner as described in Preparation Example 1 (2), indicating that 9,000 units of enzyme having an activity of 40 U/ml can be collected.

PREPARATION EXAMPLE 3

Preparation of Immobilized (R)-hydroxynitrile Lyase

The (R)-hydroxynitrile lyase enzyme solution prepared in Preparation Example 1 was subjected to ammonium sulfate precipitation to concentrate the enzyme, thereby providing a 1000 U/ml enzyme solution. Carriers for immobilization (porous silica gel; microbead silicagel 300 A, Fuji Silysia Chemical Ltd.) were mixed with this enzyme solution in an amount of 1 g per ml of enzyme solution. This mixture was used as such for the synthesis reaction. This immobilized enzyme had a water content of 50% by weight.

PREPARATION EXAMPLE 4

Preparation of Immobilized (S)-hydroxynitrile Lyase

The (S)-hydroxynitrile lyase enzyme solution prepared in Preparation Example 2 was mixed with the same carriers as used in Preparation Example 3 in an amount of 300 units per g of carrier, and then gently mixed overnight. Next, the resulting immobilized enzyme was collected by filtration and then used for the subsequent reaction. The immobilized enzyme thus prepared was measured with a Karl Fischer moisture meter, indicating that it had a water content of 50% by weight.

EXAMPLE 1

Synthesis of (R)-cyanohydrin 6 ml of 1000 U/ml (R)-hydroxynitrile lyase enzyme solution prepared from almond (*Prunus amygdalus*) was mixed with 6 g of porous silica gel (microbead silicagel 300 A, Fuji Silysia Chemical Ltd.) to prepare an immobilized enzyme. In order to examine the relationship between water content and reaction efficiency, an immobilized enzyme prepared in the same manner was dried under reduced pressure for 3 hours using an evaporator, followed by addition of 10 mM phosphate buffer (pH 5.5), to give an immobilized enzyme having an adjusted water content. In the case of Condition 4 shown in Table 1, the enzyme solution was diluted two-fold with 10 mM phosphate buffer (pH 5.5) and then immobilized on twice as much carrier as used under other conditions.

Untreated t-butyl methyl ether (TBME) used for the examination had a water content of 0.03% by weight, while TBME saturated with 10 mM phosphate buffer (pH 5.5) had a water content of 1.34% by weight. Various conditions were set up using this solvent non-saturated or saturated with the buffer to give reaction systems of varying water contents.

Under each condition, the concentrations of the substrates, 2-chlorobenzaldehyde (o-chlorobenzaldehyde) and prussic acid, were set at 1 M and 1.5 M, respectively. 600 units of each immobilized enzyme prepared above was introduced into a 10 ml reaction bottle, and then mixed with 4.143 ml of the solvent and 0.292 ml of prussic acid. 0.565 ml of 2-chlorobenzaldehyde was added to the reaction bottle to start the reaction. The reaction was carried out at 25° C. while gently stirring the reaction bottle on a bottle roller. The conditions and results are shown in Table 1.

TABLE 1

| Condition | Water content of immobilized enzyme (wt %) | Reaction solvent | Water content of reaction system* (v/v %) | Conversion ratio of aldehyde after 5 hours (mol %) |
|---|---|---|---|---|
| 1 | 0.76 | Untreated TBME | 0.96 | 6.3 |
| 2 | 0.76 | Buffer-saturated TBME | 1.86 | 6.7 |
| 3 | 50 | Buffer-saturated TBME | 12.8 | 95.3 |

TABLE 1-continued

| Condition | Water content of immobilized enzyme (wt %) | Reaction solvent | Water content of reaction system* (v/v %) | Conversion ratio of aldehyde after 5 hours (mol %) |
|---|---|---|---|---|
| 4 | 50 | Buffer-saturated TBME | 24.8 | 96.8 |

$$* \frac{\text{Water present in reaction system (vol)}}{\text{Reaction solution (organic phase) (vol)}} \times 100$$

These results indicated that a high reaction efficiency is achieved in the reaction system containing excess water as compared with the saturation amount of water in the solvent, whereas the solvent merely saturated with the buffer provides a low reaction efficiency. In Conditions 3 and 4, the liquid phase was kept as a single phase of organic solvent without two-phase separation, even though water was given in an amount far in excess of that which was soluble in the reaction solvent.

EXAMPLE 2

Since the carrier used in Preparation Example 1 could retain as much water as its weight, the enzyme was used at the same units and the carrier was used in different amounts to give reaction systems of varying water contents in order to examine the relationship between water content and reaction efficiency. The immobilized enzyme prepared as described in Preparation Example 3 was dried under reduced pressure, followed by addition of 10 mM phosphate buffer (pH 5.5), to give an immobilized enzyme having an adjusted water content for examination of the relationship between water content and reaction efficiency.

600 units of (R)-hydroxynitrile lyase was used for immobilization to prepare immobilized enzymes of varying water contents. On the other hand, prussic acid was dissolved in t-butyl methyl ether, followed by addition of 10 mM phosphate buffer (pH 5.5) in a saturation amount. Subsequently, each immobilized enzyme was mixed with the above starting material solution, followed by addition of 2-chlorobenzaldehyde. In this reaction system, the organic phase volume was 5 ml, and the concentrations of prussic acid and 2-chlorobenzaldehyde were 1.5 M and 1 M, respectively. The reaction was continued at 25° C. while gently mixing the reaction mixture. After 5 hours, the conversion ratio of 2-chlorobenzaldehyde into (R)-2-chloromandelonitrile was measured, thereby providing the result shown in FIG. 1. This result indicated that the reaction efficiency increases with increase in water content of the immobilized enzyme.

EXAMPLE 3

A solution of prussic acid (41 g) in t-butyl methyl ether (610 g) was mixed and stirred with 40 ml of 0.2 M citrate buffer (pH 7), and then allowed to stand, followed by collection of the organic phase. The immobilized (S)-hydroxynitrile lyase prepared in Preparation Example 4 (60,000 units) was added to the organic phase. At this time, the immobilized enzyme had a water content of 50% by weight. After addition of benzaldehyde (106 g), the reaction mixture was stirred to start the reaction. Reaction temperature was set at 20° C. The reaction mixture was assayed by HPLC, indicating that 126 g of (S)-mandelonitrile was produced after one hour. At this time, the conversion ratio of aldehyde was 93% and (S)-mandelonitrile had an optical purity of 99% ee. After completion of the reaction, the immobilized enzyme was recovered and repeatedly used for the reaction under the same conditions. When the reaction was repeated 16 times, (S)-mandelonitrile having an optical purity of 99% ee or more could be synthesized at an average conversion ratio of 94.2%. This indicated that the use of an immobilized enzyme having a sufficient water content achieves a highly efficient and stable synthesis of an optically active cyanohydrin.

EXAMPLE 4

Effects on an Enzyme Reaction of Reaction Inhibitors Contained in Aldehyde Compound 2-chlorobenzaldehyde containing undetectable 2-chlorobenzoic acid (reaction inhibitor) was dissolved in t-butyl methyl ether saturated with 0.15 M citrate buffer (pH 5.5) to prepare a 1 M solution of 2-chlorobenzaldehyde. To this solution, 2-chlorobenzoic acid was added in different amounts to prepare aldehyde solutions of varying 2-chlorobenzoic acid contents.

Figure 2:
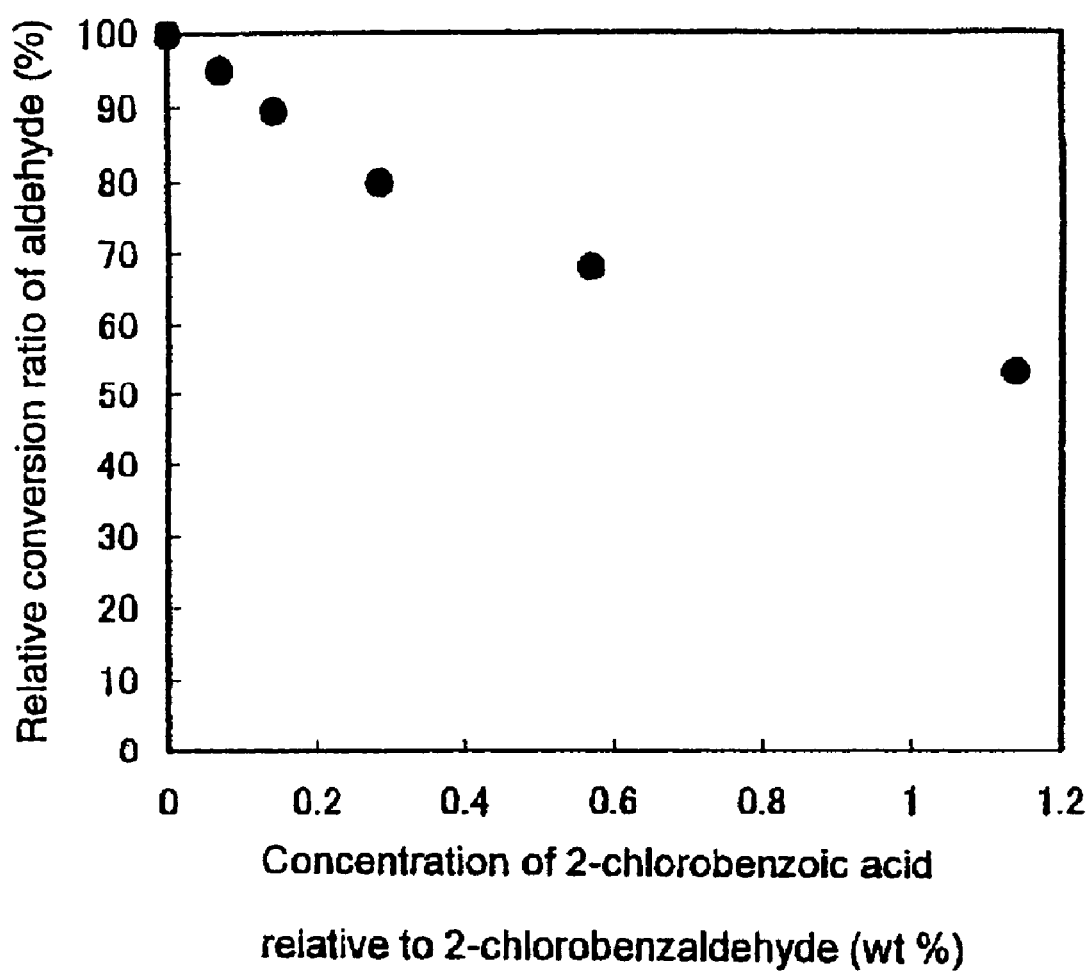
FIG. 2 shows the relationship between the conversion ratio of 2-chlorobenzaldehyde (starting material) and the concentration of 2-chlorobenzoic acid present in 2-chlorobenzaldehyde.

Immobilized (R)-hydroxynitrile lyase (600 units) was introduced into 5 mil of each solution, and prussic acid was then added to reach 1.5 M, followed by synthesis of (R)-2-chloromandelonitrile. Five hours after initiation of the reaction, an aliquot of the reaction mixture was sampled to measure the conversion ratio of aldehyde by HPLC. FIG. 2 shows the reaction rate of the reaction with the added 2-chlorobenzoic acid relative to the reaction without the added 2-chlorobenzoic acid, which is plotted against the concentration of 2-chlorobenzoic acid in 2-chlorobenzaldehyde.

As shown in FIG. 2, the enzyme reaction rate decreases with increasing concentration of 2-chlorobenzoic acid (carboxylic acid), indicating that the carboxylic acid compound acts as a reaction inhibitor. This experiment showed that the addition of 0.5 wt % and 1.1 wt % of 2-chlorobenzoic acid to 2-chlorobenzaldehyde causes about 30% and about 50% inhibition of the enzyme reaction, respectively.

EXAMPLE 5

Removal of Reaction Inhibitors by Alkaline Treatment of Aldehyde Compound

Benzaldehyde containing 0.2 wt % of benzoic acid (reaction inhibitor) was used in the alkaline treatment to perform removal of benzoic acid. Aqueous sodium hydroxide solutions of varying concentrations were prepared and mixed with the above benzaldehyde at a volume ratio of 1/1. After allowing to stand, the benzaldehyde phase was sampled to measure the benzoic acid content by HPLC.

As shown in Table 2, the alkaline treatment was found to achieve efficient removal of benzoic acid contained in benzaldehyde.

TABLE 2

| Concentration of NaOH (N) | Benzoic acid content after alkaline treatment (wt %) | Removal ratio (%) |
|---|---|---|
| 0.1 N | 0.022 | 91.0 |
| 0.01 N | 0.16 | 27.9 |
| untreated | 0.20 | |

EXAMPLE 6

Removal of Reaction Inhibitors by Alkaline Treatment of Aldehyde Compound

In a manner similar to Example 5, benzaldehyde containing 0.2 wt % of benzoic acid was used to examine the removal of benzoic acid. In this experiment, the concentration of aqueous sodium hydroxide solution was kept constant at 0.1 N, while the volume of alkaline aqueous solution to be mixed with benzaldehyde was varied.

As shown in Table 3, the alkaline treatment was found to have a sufficient effect on the removal of benzoic acid even at a volume ratio of 1:1.

TABLE 3

| Benzaldehyde:0.1 N NaOH (v:v) | Benzoic acid content after alkaline treatment (wt %) | Removal ratio (%) |
|---|---|---|
| 1:1 | 0.043 | 86.0 |
| 10:1 | 0.21 | 13.7 |
| 1:10 | 0.008 | 96.9 |
| untreated | 0.22 | |

EXAMPLE 7

Enzyme Reaction Using an Alkaline-treated Aldehyde Compound

In a manner similar to Example 6, 2-chlorobenzaldehyde was repeatedly subjected to the alkaline treatment using an equal volume of 0.1 N aqueous sodium hydroxide solution to reduce the concentration of 2-chlorobenzoic acid from 1.4 wt % to 0.03 wt % or less. This treated 2-chlorobenzaldehyde and an untreated 2-chlorobenzaldehyde originally containing 2-chlorobenzoic acid at a low concentration of 0.03 wt % or less were used as substrates to synthesize (R)-2-chloromandelonitrile.

The enzyme reaction was carried out under the same conditions as described in Example 4, except for the aldehyde compounds used. Three hours after initiation of the reaction, the conversion ratio of aldehyde was measured, indicating that both the treated and untreated aldehydes had the same conversion ratio of 69%. This showed that the alkaline treatment achieves the removal of reaction inhibitors and the same reaction efficiency as in the case where the untreated aldehyde originally containing benzoic acid at a low concentration is used.

EXAMPLE 8

Figure 3:
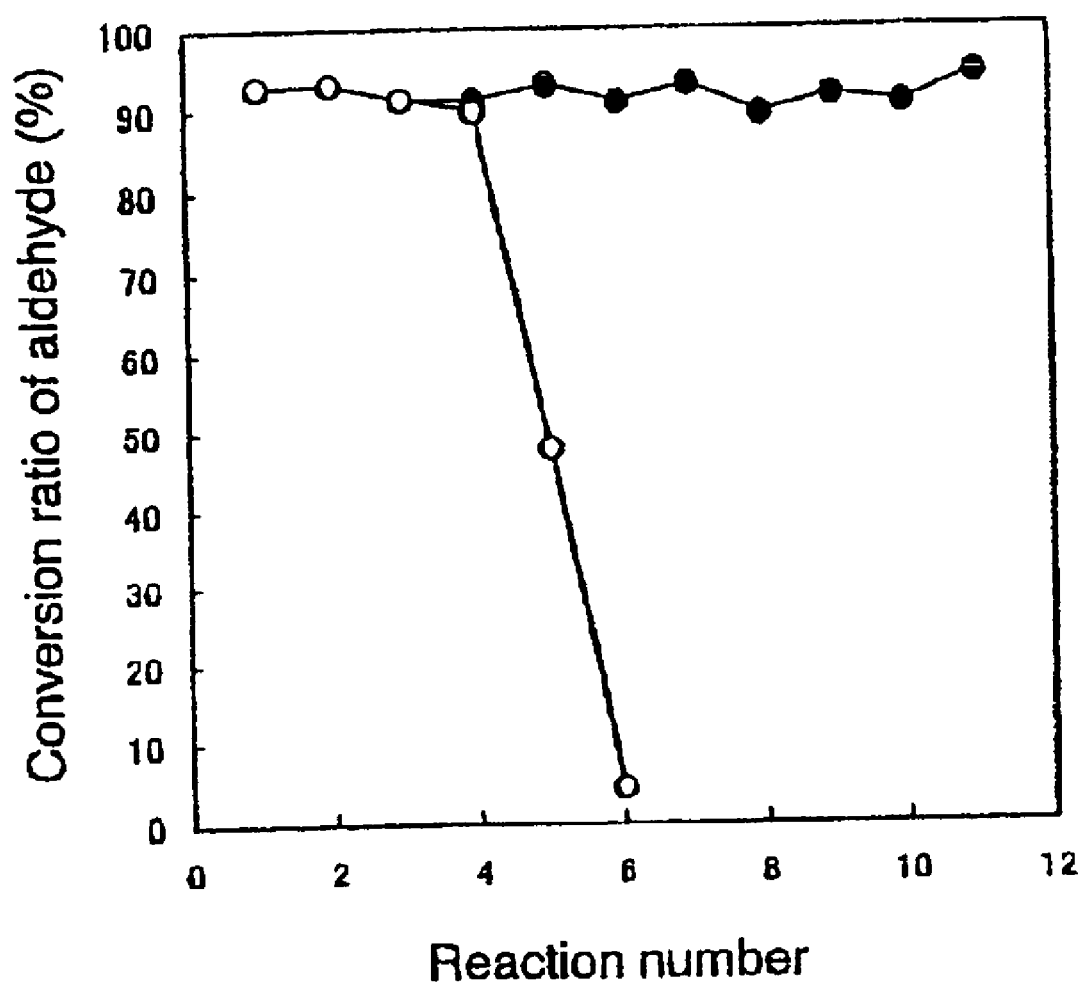
FIG. 3 shows the relationship between the conversion ratio of aldehyde and the number of times a reaction was repeated. Reference signs found in FIG. 3 have the following meanings:
- ● Example 8
- ○ Comparative Example 1

A mixture of t-butyl methyl ether (610 g) and prussic acid containing sulfurous acid as a stabilizer (41 g) was stirred and mixed with 40 ml of 0.2 M citrate buffer (pH 7). The mixture was allowed to stand, and the organic phase separated. This organic phase was mixed with the immobilized enzyme prepared in Preparation Example 4 (60,000 units), followed by addition of benzaldehyde (106 g). This reaction mixture was stirred at room temperature to synthesize (S)-mandelonitrile. After continuing the reaction for 30 minutes, the reaction solution was collected to measure the conversion ratio of aldehyde by HPLC. After completion of the reaction, the immobilized enzyme was recovered and then mixed again with a substrate solution prepared in the same manner as described above to repeat the reaction under the same conditions. As shown in FIG. 3, enzyme activity was maintained stably even though the reaction was repeated, and there was no loss of the enzyme activity even when the reaction was repeated 11 times. A 2.5 ml aliquot was taken from the 11th reaction and then mixed with 5 ml of pure water, resulting in an aqueous phase having a pH of 5.

On the other hand, prussic acid containing sulfurous acid as a stabilizer, which had been used as a starting material, was dissolved at a concentration of 1.5 M in t-butyl methyl ether, mixed with pure water at such a ratio that the mixture separated into organic and aqueous phases (organic phase: water=1:2 (v/v)), and then allowed to stand, resulting in an aqueous phase having a pH of 2.9.

COMPARATIVE EXAMPLE 1

A mixture of t-butyl methyl ether saturated with 10 mM phosphate buffer (pH 5) (610 g) and prussic acid containing sulfurous acid as a stabilizer (41 g) was mixed with the immobilized enzyme prepared in Preparation Example 4 (60,000 units), followed by addition of benzaldehyde (106 g). This reaction mixture was stirred at room temperature to synthesize (S)-mandelonitrile. After continuing the reaction for 30 minutes, the reaction solution was collected to measure the conversion ratio of aldehyde by HPLC. After completion of the reaction, the immobilized enzyme was recovered and then mixed again with a substrate solution prepared in the same manner as described above to repeat the reaction under the same conditions. As shown in FIG. 3, enzyme activity significantly decreased when the reaction was repeated 5 times, and was almost completely lost at the 6th reaction. A 2.5 ml aliquot was taken from the 6th reaction and then mixed with 5 ml of pure water, resulting in an aqueous phase having a pH reduced to 3.5.

EXAMPLE 9

In a manner similar to Example 7, benzaldehyde was subjected to the alkaline treatment using an equal volume of 0.1 N aqueous sodium hydroxide solution. This treated benzaldehyde was used to synthesize (S)-mandelonitrile by repeatedly using the immobilized enzyme in the same manner as described in Example 8. After completion of each batch reaction, the reaction solution was collected and then mixed with p-toluenesulfonic acid monohydrate (stabilizer) in an amount of 2.7 g per liter of reaction solution. Each solution was then distilled under reduced pressure at 50 torr and at 45° C. to collect t-butyl methyl ether (solvent) and unreacted prussic acid from the solution.

This experiment showed that 85% or more of t-butyl methyl ether and prussic acid can be collected even though the distillation was carried out under such conditions.

Further, additional prussic acid was added to the collected t-butyl methyl ether containing prussic acid to prepare a 1.5 M prussic acid solution in t-butyl methyl ether. This solution was treated in the same manner as described in Example 3 and then used to synthesize (S)-mandelonitrile. The result was shown in FIG. 4. The first three batch reactions used fresh t-butyl methyl ether and prussic acid, while other batch reactions used a recycled prussic acid solution in t-butyl methyl ether which had been prepared by collecting t-butyl methyl ether containing prussic acid through the above distillation process, supplying it with fresh prussic acid in order to adjust the concentration of prussic acid, and then treating it in the same manner as described in Example 3.

As shown in FIG. 4, the use of the recycled t-butyl methyl ether and prussic acid has no adverse effect on the enzyme reaction and can provide the same result as in the case where fresh prussic acid and t-butyl methyl ether are used.

All the publications, patents and patent applications cited herein are incorporated herein by reference in their entirety.

What is claimed is:

1. A method for producing an optically active cyanohydrin comprising:

adding hydrogen cyanide and either water or an acqueous buffer to an organic solvent that is substantially immiscible with water to form an organic solvent which comprises hydrogen cyanide and is saturated with water; and forming a reaction composition comprising an immobilized hydroxynitrile lyase having a water content of 10% or more by weight, and a liquid comprising a carbonyl compound and the organic solvent which comprises hydrogen cyanide and is saturated with water, wherein the liquid is a uniform liquid phase without phase separation.

2. The method of claim 1, wherein the immobilized hydroxynitrile lyase is immobilized on a carrier that is capable of retaining water.

3. The method of claim 1, wherein the liquid is saturated with water or aqueous buffer sufficient to prevent release of water from the immobilized hydroxynitrile lyase.

4. The method of claim 1, wherein the organic solvent which comprises hydrogen cyanide and is saturated with water, is formed by adding hydrogen cyanide to the organic solvent that is substantially immiscible with water, and saturating the organic solvent comprising hydrogen cyanide with water or an aqueous buffer.

* * * * *

UNITED STATES PATENT AND TRADEMARK OFFICE
CERTIFICATE OF CORRECTION

PATENT NO. : 7,078,225 B2
APPLICATION NO. : 09/870821
DATED : July 18, 2006
INVENTOR(S) : Hisashi Semba and Yukio Dobashi It is certified that error appears in the above-identified patent and that said Letters Patent is hereby corrected as shown below:

On the title page, item (54), and Column 1, the title, "METHOD FOR ENZYMATICALLY PRODUCING AN OPTICALLY ACTIVE CYANOHYDRIN " should read --ENZYME REACTION METHOD AND A METHOD FOR ENZYMATICALLY PRODUCING AN OPTICALLY ACTIVE CYANOHYDRIN--.

On the title page, item (56), under "OTHER PUBLICATIONS," the first citation, "Dove, S. et al., 7-Substituted-4-hydroxyquinoline-3-carboxylic Acids as Inhibitors of Dehydrogenase Enzymes and of the Respiration of Ehrlich Ascites Tumor Cells: Multi-varite Analysis and Quantitlative Structure-Activity Relationship for Polar Substituents, J. Med. Chem., 1985, vol. 28, pp. 447-451." should read --Dove, S. et al., 7-Substituted-4-hydroxyquinoline-3-carboxylic Acids as Inhibitors of Dehydrogenase Enzymes and of the Respiration of Ehrlich Ascites Tumor Cells: Multi-varite Analysis and Quantitative Structure-Activity Relationship for Polar Substituents, J. Med. Chem., 1985, vol. 28, pp. 447-451.--

On the title page, item (56), under "OTHER PUBLICATIONS," the third citation, "Loos et al. "Synthesis of Optically Active Cyanohydrins Using R-Oxynitrilase in a Liquid-Liquid Biphasic System," Biocatalysis and Biotransformation, vol. 12, 255-266 (1955)." should read --Loos et al. "Synthesis of Optically Active Cyanohydrins Using R-Oxynitrilase in a Liquid-Liquid Biphasic System," Biocatalysis and Biotransformation, vol. 12, 255-266 (1995).--

In claim 1, column 31, line 12, "acqueous" should read --aqueous--.

Signed and Sealed this

Twenty-third Day of January, 2007

JON W. DUDAS
*Director of the United States Patent and Trademark Office*